US008955518B2

(12) United States Patent
Wondka

(10) Patent No.: US 8,955,518 B2
(45) Date of Patent: Feb. 17, 2015

(54) METHODS, SYSTEMS AND DEVICES FOR IMPROVING VENTILATION IN A LUNG AREA

(75) Inventor: Anthony D. Wondka, Thousand Oaks, CA (US)

(73) Assignee: Breathe Technologies, Inc., Irvine, CA (US)

( * ) Notice: Subject to any disclaimer, the term of this patent is extended or adjusted under 35 U.S.C. 154(b) by 248 days.

(21) Appl. No.: 13/365,917

(22) Filed: Feb. 3, 2012

(65) Prior Publication Data

US 2013/0019864 A1    Jan. 24, 2013

Related U.S. Application Data

(63) Continuation of application No. 12/493,677, filed on Jun. 29, 2009, now abandoned, which is a continuation of application No. 10/870,849, filed on Jun. 17, 2004, now Pat. No. 7,588,033.

(60) Provisional application No. 60/479,213, filed on Jun. 18, 2003.

(51) Int. Cl.
*A61M 11/00*    (2006.01)
*A61M 16/10*    (2006.01)
(Continued)

(52) U.S. Cl.
CPC ............... *A61M 16/10* (2013.01); *A61M 16/04* (2013.01); *A61M 16/0009* (2013.01);
(Continued)

(58) Field of Classification Search
USPC ............. 128/200.26, 207.14, 207.15, 207.16; 604/516, 518, 514, 509, 48, 28, 35; 424/423; 607/99; 600/114, 116; 606/108
See application file for complete search history.

(56) References Cited

U.S. PATENT DOCUMENTS

| 50,641 | A | 10/1865 | Stone |
|---|---|---|---|
| 428,592 | A | 5/1890 | Chapman |

(Continued)

FOREIGN PATENT DOCUMENTS

| CN | 1750854 | 3/2006 |
|---|---|---|
| DE | 19626924 | 1/1998 |

(Continued)

OTHER PUBLICATIONS

In the U.S. Patent and Trademark Office, Supplemental Notice of Allowance dated in re: U.S. Appl. No. 10/771,803, dated Dec. 2, 2008, 2 pages.
(Continued)

*Primary Examiner* — Steven Douglas
(74) *Attorney, Agent, or Firm* — Stetina Brunda Garred & Brucker

(57) ABSTRACT

Methods, systems and devices are described for new modes of ventilation in which specific lung areas are ventilated with an indwelling trans-tracheobronchial catheter for the purpose of improving ventilation and reducing hyperinflation in that specific lung area, and for redirecting inspired air to other healthier lung areas. Trans-tracheobronchial Segmental Ventilation (TTSV) is performed on either a naturally breathing or a mechanical ventilated, patient by placing a uniquely configured indwelling catheter into a bronchus of a poorly ventilated specific lung area and providing direct ventilation to that area. Typically the catheter's distal tip is anchored without occluding the bronchus. TTSV is optionally performed by insufflation only of the area, or by the application of vacuum to the area, can include elevating or reducing the pressure in the targeted area to facilitate stagnant gas removal, or can include blocking the area to divert inspired gas to better functioning areas.

22 Claims, 12 Drawing Sheets

(51) Int. Cl.
  *A61M 16/04* (2006.01)
  *A61M 16/00* (2006.01)
  *A61M 16/06* (2006.01)

(52) U.S. Cl.
  CPC ........ *A61M 16/0404* (2013.01); *A61M 16/042* (2013.01); *A61M 16/0445* (2013.01); *A61M 16/0459* (2013.01); *A61M 16/0486* (2013.01); *A61M 16/0672* (2013.01); *A61M 16/0434* (2013.01); *A61M 16/0465* (2013.01); *A61M 2016/0021* (2013.01); *A61M 2205/8225* (2013.01); *A61M 2209/06* (2013.01); *A61M 2230/432* (2013.01)
  USPC .................... 128/207.14; 128/200.26; 604/35

(56) References Cited

U.S. PATENT DOCUMENTS

| | | |
|---|---|---|
| 697,181 A | 4/1902 | Smith |
| 718,785 A | 1/1903 | McNary |
| 853,439 A | 5/1907 | Clark |
| 859,156 A | 7/1907 | Warnken |
| 909,002 A | 1/1909 | Lambert |
| 1,125,542 A | 1/1915 | Humphries |
| 1,129,619 A | 2/1915 | Zapf |
| 1,331,297 A | 2/1920 | Walker |
| 2,178,800 A | 11/1939 | Lombard |
| 2,259,817 A | 10/1941 | Hawkins |
| 2,552,595 A | 5/1951 | Seeler |
| 2,663,297 A | 12/1953 | Turnberg |
| 2,693,800 A | 11/1954 | Caldwell |
| 2,735,432 A | 2/1956 | Hudson |
| 2,792,000 A | 5/1957 | Richardson |
| 2,843,122 A | 7/1958 | Hudson |
| 2,859,748 A | 11/1958 | Hudson |
| 2,931,358 A | 4/1960 | Sheridan |
| 2,947,938 A | 8/1960 | Bennett |
| 3,172,407 A | 3/1965 | Von Pechmann |
| 3,267,935 A | 8/1966 | Andreasen et al. |
| 3,319,627 A | 5/1967 | Windsor |
| 3,357,424 A | 12/1967 | Schreiber |
| 3,357,427 A | 12/1967 | Wittke et al. |
| 3,357,428 A | 12/1967 | Carlson |
| 3,437,274 A | 4/1969 | Apri |
| 3,460,533 A | 8/1969 | Riú Piá |
| 3,493,703 A | 2/1970 | Finan |
| 3,513,844 A | 5/1970 | Smith |
| 3,610,247 A | 10/1971 | Jackson |
| 3,625,206 A | 12/1971 | Charnley |
| 3,625,207 A | 12/1971 | Agnew |
| 3,631,438 A | 12/1971 | Lewin |
| 3,643,660 A | 2/1972 | Hudson et al. |
| 3,657,740 A | 4/1972 | Cialone |
| 3,682,171 A | 8/1972 | Dali et al. |
| 3,721,233 A | 3/1973 | Montgomery et al. |
| 3,726,275 A | 4/1973 | Jackson et al. |
| 3,727,606 A | 4/1973 | Sielaff |
| 3,733,008 A | 5/1973 | Churchill et al. |
| 3,741,208 A | 6/1973 | Jonsson et al. |
| 3,754,552 A | 8/1973 | King |
| 3,794,026 A | 2/1974 | Jacobs |
| 3,794,072 A | 2/1974 | Diedrich et al. |
| 3,802,431 A | 4/1974 | Farr |
| 3,831,596 A | 8/1974 | Cavallo |
| 3,881,480 A | 5/1975 | Lafourcade |
| 3,896,800 A | 7/1975 | Cibulka |
| 3,903,881 A | 9/1975 | Weigl |
| 3,905,362 A | 9/1975 | Eyrick et al. |
| 3,949,749 A | 4/1976 | Stewart |
| 3,951,143 A | 4/1976 | Kitrilakis et al. |
| 3,961,627 A | 6/1976 | Ernst et al. |
| 3,972,327 A | 8/1976 | Ernst et al. |
| 3,985,131 A | 10/1976 | Buck et al. |
| 3,991,790 A | 11/1976 | Russell |
| 4,003,377 A | 1/1977 | Dahl |
| 4,036,253 A | 7/1977 | Fegan et al. |
| 4,054,133 A | 10/1977 | Myers |
| 4,067,328 A | 1/1978 | Manley |
| 4,106,505 A | 8/1978 | Salter et al. |
| 4,146,885 A | 3/1979 | Lawson, Jr. |
| 4,206,754 A | 6/1980 | Cox et al. |
| 4,211,086 A | 7/1980 | Leonard et al. |
| 4,216,769 A | 8/1980 | Grimes |
| 4,231,363 A | 11/1980 | Grimes |
| 4,231,365 A | 11/1980 | Scarberry |
| 4,232,665 A | 11/1980 | Vaseen |
| 4,256,101 A | 3/1981 | Ellestad |
| 4,261,355 A | 4/1981 | Glazener |
| 4,263,908 A | 4/1981 | Mizerak |
| 4,265,237 A | 5/1981 | Schwanbom et al. |
| 4,266,540 A | 5/1981 | Panzik et al. |
| 4,273,124 A | 6/1981 | Zimmerman |
| 4,274,162 A | 6/1981 | Joy et al. |
| 4,278,082 A | 7/1981 | Blackmer |
| 4,282,869 A | 8/1981 | Zidulka |
| 4,306,567 A | 12/1981 | Krasner |
| 4,323,064 A | 4/1982 | Hoenig et al. |
| 4,354,488 A | 10/1982 | Bartos |
| 4,365,636 A | 12/1982 | Barker |
| 4,367,735 A | 1/1983 | Dali |
| 4,377,162 A | 3/1983 | Staver |
| 4,393,869 A | 7/1983 | Boyarsky et al. |
| 4,406,283 A | 9/1983 | Bir |
| 4,411,267 A | 10/1983 | Heyman |
| 4,413,514 A | 11/1983 | Bowman |
| 4,421,113 A | 12/1983 | Gedeon et al. |
| 4,422,456 A | 12/1983 | Tiep |
| 4,449,523 A | 5/1984 | Szachowicz et al. |
| 4,454,880 A | 6/1984 | Muto et al. |
| 4,462,398 A | 7/1984 | Durkan et al. |
| 4,469,097 A | 9/1984 | Kelman |
| 4,481,944 A | 11/1984 | Bunnell |
| 4,488,548 A | 12/1984 | Agdanowski |
| 4,495,946 A | 1/1985 | Lemer |
| 4,506,666 A | 3/1985 | Durkan |
| 4,506,667 A | 3/1985 | Ansite |
| 4,519,387 A | 5/1985 | Durkan et al. |
| 4,520,812 A | 6/1985 | Freitag et al. |
| 4,527,557 A | 7/1985 | DeVries et al. |
| 4,535,766 A | 8/1985 | Baum |
| 4,537,188 A | 8/1985 | Phuc |
| 4,539,984 A | 9/1985 | Kiszel et al. |
| 4,548,590 A | 10/1985 | Green |
| 4,559,940 A | 12/1985 | McGinnis |
| 4,570,631 A | 2/1986 | Durkan |
| 4,571,741 A | 2/1986 | Guillaumot |
| 4,584,996 A | 4/1986 | Blum |
| 4,590,951 A | 5/1986 | O'Connor |
| 4,592,349 A | 6/1986 | Bird |
| 4,621,632 A | 11/1986 | Bartels et al. |
| 4,630,606 A | 12/1986 | Weerda et al. |
| 4,630,614 A | 12/1986 | Atlas |
| 4,644,947 A | 2/1987 | Whitwam et al. |
| 4,648,395 A | 3/1987 | Sato et al. |
| 4,648,398 A | 3/1987 | Agdanowski et al. |
| 4,658,832 A | 4/1987 | Brugnoli |
| 4,660,555 A | 4/1987 | Payton |
| 4,682,591 A | 7/1987 | Jones |
| 4,684,398 A | 8/1987 | Dunbar et al. |
| 4,686,974 A | 8/1987 | Sato et al. |
| 4,686,975 A | 8/1987 | Naimon et al. |
| 4,688,961 A | 8/1987 | Shioda et al. |
| 4,705,034 A | 11/1987 | Perkins |
| 4,744,356 A | 5/1988 | Greenwood |
| 4,747,403 A | 5/1988 | Gluck et al. |
| 4,753,233 A | 6/1988 | Grimes |
| 4,773,411 A | 9/1988 | Downs |
| 4,776,333 A | 10/1988 | Miyamae |
| 4,782,832 A | 11/1988 | Trimble et al. |
| 4,784,130 A | 11/1988 | Kenyon et al. |
| 4,803,981 A | 2/1989 | Vickery |
| 4,807,616 A | 2/1989 | Adahan |
| 4,807,617 A | 2/1989 | Nesti |
| 4,808,160 A | 2/1989 | Timmons et al. |

(56) References Cited

U.S. PATENT DOCUMENTS

| | | |
|---|---|---|
| 4,813,431 A | 3/1989 | Brown |
| 4,817,897 A | 4/1989 | Kreusel |
| 4,818,320 A | 4/1989 | Weichselbaum |
| 4,823,788 A | 4/1989 | Smith et al. |
| 4,825,859 A | 5/1989 | Lambert |
| 4,827,922 A | 5/1989 | Champain et al. |
| 4,832,014 A | 5/1989 | Perkins |
| 4,838,255 A | 6/1989 | Lambert |
| 4,841,953 A | 6/1989 | Dodrill |
| 4,848,333 A | 7/1989 | Waite |
| 4,850,350 A | 7/1989 | Jackson |
| 4,865,586 A | 9/1989 | Hedberg |
| 4,869,718 A | 9/1989 | Brader |
| 4,899,740 A | 2/1990 | Napolitano |
| 4,905,688 A | 3/1990 | Vicenzi et al. |
| 4,915,103 A | 4/1990 | Visveshwara et al. |
| 4,915,105 A | 4/1990 | Lee |
| 4,919,128 A | 4/1990 | Kopala et al. |
| 4,919,132 A | 4/1990 | Miser |
| 4,938,212 A | 7/1990 | Snook et al. |
| 4,944,310 A | 7/1990 | Sullivan |
| 4,967,743 A | 11/1990 | Lambert |
| 4,971,049 A | 11/1990 | Rotariu et al. |
| 4,982,735 A | 1/1991 | Yagata et al. |
| 4,986,269 A | 1/1991 | Hakkinen |
| 4,989,599 A | 2/1991 | Carter |
| 4,990,157 A | 2/1991 | Roberts et al. |
| 5,000,175 A | 3/1991 | Pue |
| 5,002,050 A | 3/1991 | McGinnis |
| 5,005,570 A | 4/1991 | Perkins |
| 5,018,519 A | 5/1991 | Brown |
| 5,022,394 A | 6/1991 | Chmielinski |
| 5,024,219 A | 6/1991 | Dietz |
| 5,025,805 A | 6/1991 | Nutter |
| 5,038,771 A | 8/1991 | Dietz |
| 5,042,478 A | 8/1991 | Kopala et al. |
| 5,046,491 A | 9/1991 | Derrick |
| 5,046,492 A | 9/1991 | Stackhouse et al. |
| 5,048,515 A | 9/1991 | Sanso |
| 5,048,516 A | 9/1991 | Soderberg |
| 5,052,400 A | 10/1991 | Dietz |
| 5,054,484 A | 10/1991 | Hebeler, Jr. |
| 5,058,580 A | 10/1991 | Hazard |
| 5,074,299 A | 12/1991 | Dietz |
| 5,076,267 A | 12/1991 | Pasternack |
| 5,090,408 A | 2/1992 | Spofford et al. |
| 5,097,827 A | 3/1992 | Izumi |
| 5,099,836 A | 3/1992 | Rowland et al. |
| 5,099,837 A | 3/1992 | Russel, Sr. et al. |
| 5,101,820 A | 4/1992 | Christopher |
| 5,103,815 A | 4/1992 | Siegel et al. |
| 5,105,807 A | 4/1992 | Kahn et al. |
| 5,107,830 A | 4/1992 | Younes |
| 5,107,831 A | 4/1992 | Halpern et al. |
| 5,113,857 A | 5/1992 | Dickerman et al. |
| 5,117,818 A | 6/1992 | Palfy |
| 5,117,819 A | 6/1992 | Servidio et al. |
| 5,127,400 A | 7/1992 | DeVries et al. |
| 5,134,995 A | 8/1992 | Gruenke et al. |
| 5,134,996 A | 8/1992 | Bell |
| 5,140,045 A | 8/1992 | Askanazi et al. |
| 5,148,802 A | 9/1992 | Sanders et al. |
| 5,161,525 A | 11/1992 | Kimm et al. |
| 5,165,397 A | 11/1992 | Arp |
| 5,181,509 A | 1/1993 | Spofford et al. |
| 5,184,610 A | 2/1993 | Marten et al. |
| 5,186,167 A | 2/1993 | Kolobow |
| 5,188,592 A * | 2/1993 | Hakki ............................ 604/35 |
| 5,193,532 A | 3/1993 | Moa et al. |
| 5,193,533 A | 3/1993 | Body et al. |
| 5,199,424 A | 4/1993 | Sullivan et al. |
| 5,211,170 A | 5/1993 | Press |
| 5,217,008 A | 6/1993 | Lindholm |
| 5,233,978 A | 8/1993 | Callaway |
| 5,233,979 A | 8/1993 | Strickland |
| 5,239,994 A | 8/1993 | Atkins |
| 5,239,995 A | 8/1993 | Estes et al. |
| 5,243,972 A | 9/1993 | Huang |
| 5,245,995 A | 9/1993 | Sullivan et al. |
| 5,255,675 A | 10/1993 | Kolobow |
| 5,258,027 A | 11/1993 | Berghaus |
| 5,269,296 A | 12/1993 | Landis |
| 5,271,388 A | 12/1993 | Whitwam et al. |
| 5,271,391 A | 12/1993 | Graves |
| 5,275,159 A | 1/1994 | Griebel |
| 5,279,288 A | 1/1994 | Christopher |
| 5,287,852 A | 2/1994 | Arkinstall |
| 5,303,698 A | 4/1994 | Tobia et al. |
| 5,303,700 A | 4/1994 | Weismann et al. |
| 5,318,019 A | 6/1994 | Celaya |
| 5,331,995 A | 7/1994 | Westfall et al. |
| 5,335,656 A | 8/1994 | Bowe et al. |
| 5,339,809 A | 8/1994 | Beck, Jr. et al. |
| 5,349,946 A | 9/1994 | McComb |
| 5,365,922 A | 11/1994 | Raemer |
| 5,368,017 A | 11/1994 | Sorenson et al. |
| 5,370,112 A | 12/1994 | Perkins |
| 5,373,842 A | 12/1994 | Olsson et al. |
| 5,375,593 A | 12/1994 | Press |
| 5,388,575 A | 2/1995 | Taube |
| 5,394,870 A | 3/1995 | Johansson |
| 5,398,676 A | 3/1995 | Press et al. |
| 5,398,682 A | 3/1995 | Lynn |
| 5,400,778 A | 3/1995 | Jonson et al. |
| 5,419,314 A | 5/1995 | Christopher |
| 5,438,979 A | 8/1995 | Johnson, Jr. et al. |
| 5,438,980 A | 8/1995 | Phillips |
| 5,443,075 A | 8/1995 | Holscher |
| 5,460,174 A | 10/1995 | Chang |
| 5,460,613 A | 10/1995 | Ulrich et al. |
| 5,474,062 A | 12/1995 | DeVires et al. |
| 5,477,852 A | 12/1995 | Landis et al. |
| 5,485,850 A | 1/1996 | Dietz |
| 5,490,502 A | 2/1996 | Rapoport et al. |
| 5,503,146 A | 4/1996 | Froehlich et al. |
| 5,503,497 A | 4/1996 | Dudley et al. |
| 5,507,282 A | 4/1996 | Younes |
| 5,509,409 A | 4/1996 | Weatherholt |
| 5,511,542 A | 4/1996 | Hall |
| 5,513,628 A | 5/1996 | Coles et al. |
| 5,513,631 A | 5/1996 | McWilliams |
| 5,513,635 A | 5/1996 | Bedi |
| 5,522,382 A | 6/1996 | Sullivan et al. |
| 5,526,806 A | 6/1996 | Sansoni |
| 5,529,060 A | 6/1996 | Salmon et al. |
| 5,533,506 A | 7/1996 | Wood |
| 5,535,738 A | 7/1996 | Estes et al. |
| 5,537,997 A | 7/1996 | Mechlenburg et al. |
| 5,538,002 A | 7/1996 | Boussignac et al. |
| 5,542,415 A | 8/1996 | Brody |
| 5,546,935 A | 8/1996 | Champeau |
| 5,549,106 A | 8/1996 | Gruenke et al. |
| 5,551,419 A | 9/1996 | Froehlich et al. |
| 5,558,086 A | 9/1996 | Smith et al. |
| 5,564,416 A | 10/1996 | Jones |
| 5,575,282 A | 11/1996 | Knoch et al. |
| 5,582,164 A | 12/1996 | Sanders |
| 5,593,143 A | 1/1997 | Ferrarin |
| 5,595,174 A | 1/1997 | Gwaltney |
| 5,598,837 A | 2/1997 | Sirianne, Jr. et al. |
| 5,598,840 A | 2/1997 | Iund et al. |
| 5,603,315 A | 2/1997 | Sasso, Jr. |
| 5,605,148 A | 2/1997 | Jones |
| 5,626,131 A | 5/1997 | Chua et al. |
| 5,632,269 A | 5/1997 | Zdrojkowski |
| 5,636,630 A | 6/1997 | Miller et al. |
| 5,645,053 A | 7/1997 | Remmers et al. |
| 5,645,054 A | 7/1997 | Cotner et al. |
| 5,647,351 A | 7/1997 | Weismann et al. |
| 5,669,377 A | 9/1997 | Fenn |
| 5,669,380 A | 9/1997 | Garry et al. |
| 5,676,132 A | 10/1997 | Tillotson et al. |
| 5,676,135 A | 10/1997 | McClean |
| 5,682,878 A | 11/1997 | Ogden |

(56) References Cited

U.S. PATENT DOCUMENTS

| | | |
|---|---|---|
| 5,682,881 A | 11/1997 | Winthrop et al. |
| 5,687,713 A | 11/1997 | Bahr et al. |
| 5,687,714 A | 11/1997 | Kolobow et al. |
| 5,687,715 A | 11/1997 | Landis et al. |
| 5,690,097 A | 11/1997 | Howard et al. |
| 5,692,497 A | 12/1997 | Schnitzer et al. |
| 5,697,364 A | 12/1997 | Chua et al. |
| 5,704,345 A | 1/1998 | Berthon-Jones |
| 5,711,296 A | 1/1998 | Kolobow |
| 5,715,812 A | 2/1998 | Deighan et al. |
| 5,715,815 A | 2/1998 | Lorenzen et al. |
| 5,720,278 A | 2/1998 | Lachmann et al. |
| 5,735,268 A | 4/1998 | Chua et al. |
| 5,735,272 A | 4/1998 | Dillon et al. |
| 5,740,796 A | 4/1998 | Skog |
| 5,752,511 A | 5/1998 | Simmons et al. |
| 5,762,638 A | 6/1998 | Shikani et al. |
| 5,791,337 A | 8/1998 | Coles et al. |
| 5,819,723 A | 10/1998 | Joseph |
| 5,826,579 A | 10/1998 | Remmers et al. |
| 5,845,636 A | 12/1998 | Gruenke et al. |
| 5,865,173 A | 2/1999 | Froehlich |
| 5,865,174 A | 2/1999 | Kloeppel |
| 5,881,723 A | 3/1999 | Wallace et al. |
| 5,896,857 A | 4/1999 | Hely et al. |
| 5,904,648 A | 5/1999 | Arndt et al. |
| 5,906,204 A | 5/1999 | Beran et al. |
| 5,911,756 A | 6/1999 | Debry |
| 5,915,379 A | 6/1999 | Wallace et al. |
| 5,915,381 A | 6/1999 | Nord |
| 5,918,597 A | 7/1999 | Jones et al. |
| 5,921,238 A | 7/1999 | Bourdon |
| 5,921,942 A | 7/1999 | Remmers et al. |
| 5,921,952 A | 7/1999 | Desmond, III et al. |
| 5,927,276 A | 7/1999 | Rodriguez |
| 5,927,400 A | 7/1999 | Bononi et al. |
| 5,928,189 A | 7/1999 | Phillips et al. |
| 5,931,160 A | 8/1999 | Gilmore et al. |
| 5,931,162 A | 8/1999 | Christian |
| 5,937,853 A | 8/1999 | Strom |
| 5,937,855 A | 8/1999 | Zdrojkowski et al. |
| 5,938,118 A | 8/1999 | Cooper |
| 5,954,050 A | 9/1999 | Christopher |
| 5,957,136 A | 9/1999 | Magidson et al. |
| 5,964,223 A | 10/1999 | Baran |
| 5,975,077 A | 11/1999 | Hofstetter et al. |
| 5,975,081 A | 11/1999 | Hood et al. |
| 5,979,440 A | 11/1999 | Honkonen et al. |
| 5,989,193 A | 11/1999 | Sullivan |
| 6,000,396 A | 12/1999 | Melker et al. |
| 6,019,101 A | 2/2000 | Cotner et al. |
| 6,039,696 A | 3/2000 | Bell |
| 6,050,260 A | 4/2000 | Daniell et al. |
| 6,076,519 A | 6/2000 | Johnson |
| 6,085,747 A | 7/2000 | Axe et al. |
| 6,091,973 A | 7/2000 | Colla et al. |
| 6,093,169 A | 7/2000 | Cardoso |
| 6,095,505 A | 8/2000 | Miller |
| 6,105,575 A | 8/2000 | Estes et al. |
| 6,109,264 A | 8/2000 | Sauer |
| 6,112,746 A | 9/2000 | Kwok et al. |
| 6,119,694 A | 9/2000 | Correa et al. |
| 6,120,460 A | 9/2000 | Abreu |
| 6,123,668 A | 9/2000 | Abreu |
| 6,131,571 A | 10/2000 | Lampotang et al. |
| 6,135,970 A | 10/2000 | Kadhiresan et al. |
| 6,152,132 A | 11/2000 | Psaros |
| 6,152,134 A | 11/2000 | Webber et al. |
| 6,158,432 A | 12/2000 | Biondi et al. |
| 6,192,883 B1 | 2/2001 | Miller, Jr. |
| 6,203,502 B1 | 3/2001 | Hilgendorf et al. |
| 6,213,119 B1 | 4/2001 | Brydon et al. |
| 6,213,955 B1 | 4/2001 | Karakasoglu et al. |
| 6,220,244 B1 | 4/2001 | McLaughlin |
| 6,224,560 B1 | 5/2001 | Gazula et al. |
| 6,227,200 B1 | 5/2001 | Crump et al. |
| 6,247,470 B1 | 6/2001 | Ketchedjian |
| 6,269,811 B1 | 8/2001 | Duff et al. |
| 6,269,812 B1 | 8/2001 | Wallace et al. |
| 6,273,859 B1 | 8/2001 | Remmers et al. |
| 6,286,508 B1 | 9/2001 | Remmers et al. |
| D449,376 S | 10/2001 | McDonald et al. |
| D449,883 S | 10/2001 | McDonald et al. |
| 6,298,850 B1 | 10/2001 | Argraves |
| 6,305,374 B1 | 10/2001 | Zdrojkowski et al. |
| 6,314,957 B1 | 11/2001 | Boissin et al. |
| 6,315,739 B1 | 11/2001 | Merilainen et al. |
| D451,598 S | 12/2001 | McDonald et al. |
| 6,328,038 B1 | 12/2001 | Kessler et al. |
| 6,328,753 B1 | 12/2001 | Zammit |
| 6,332,463 B1 | 12/2001 | Farrugia et al. |
| 6,345,619 B1 | 2/2002 | Finn |
| 6,357,438 B1 | 3/2002 | Hansen |
| 6,357,440 B1 | 3/2002 | Hansen et al. |
| 6,360,741 B2 | 3/2002 | Truschel |
| 6,360,745 B1 | 3/2002 | Wallace et al. |
| 6,363,933 B1 | 4/2002 | Berthon-Jones |
| 6,367,474 B1 | 4/2002 | Berthon-Jones et al. |
| 6,369,838 B1 | 4/2002 | Wallace et al. |
| 6,371,114 B1 | 4/2002 | Schmidt et al. |
| 6,378,520 B1 | 4/2002 | Davenport |
| 6,390,091 B1 | 5/2002 | Banner et al. |
| 6,394,088 B1 | 5/2002 | Frye et al. |
| 6,398,739 B1 | 6/2002 | Sullivan et al. |
| 6,418,928 B1 | 7/2002 | Bordewick et al. |
| 6,422,240 B1 | 7/2002 | Levitsky et al. |
| 6,423,001 B1 | 7/2002 | Abreu |
| 6,427,690 B1 | 8/2002 | McCombs et al. |
| 6,431,172 B1 | 8/2002 | Bordewick |
| 6,439,228 B1 | 8/2002 | Hete et al. |
| 6,439,229 B1 | 8/2002 | Du et al. |
| 6,439,234 B1 | 8/2002 | Curti et al. |
| 6,439,235 B1 | 8/2002 | Larquet et al. |
| 6,450,164 B1 | 9/2002 | Banner et al. |
| 6,450,166 B1 | 9/2002 | McDonald et al. |
| 6,457,472 B1 | 10/2002 | Schwartz et al. |
| 6,467,477 B1 | 10/2002 | Frank et al. |
| 6,478,026 B1 | 11/2002 | Wood |
| 6,494,202 B2 | 12/2002 | Farmer |
| 6,494,206 B1 | 12/2002 | Bergamaschi et al. |
| 6,505,623 B1 | 1/2003 | Hansen |
| 6,505,624 B1 | 1/2003 | Campbell, Sr. |
| 6,516,801 B2 | 2/2003 | Boussignac |
| 6,520,176 B1 | 2/2003 | Dubois et al. |
| 6,520,183 B2 | 2/2003 | Amar |
| 6,530,373 B1 | 3/2003 | Patron et al. |
| 6,532,958 B1 | 3/2003 | Buan et al. |
| 6,532,960 B1 | 3/2003 | Yurko |
| 6,536,432 B2 | 3/2003 | Truschel |
| 6,536,436 B1 | 3/2003 | McGlothen |
| 6,550,478 B2 | 4/2003 | Remmers et al. |
| 6,553,992 B1 | 4/2003 | Berthon-Jones et al. |
| 6,561,188 B1 | 5/2003 | Ellis |
| 6,561,193 B1 | 5/2003 | Noble |
| 6,564,797 B1 | 5/2003 | Mechlenburg et al. |
| 6,564,800 B1 | 5/2003 | Olivares |
| 6,568,391 B1 | 5/2003 | Tatarek et al. |
| 6,571,794 B1 | 6/2003 | Hansen |
| 6,571,796 B2 | 6/2003 | Banner et al. |
| 6,571,798 B1 | 6/2003 | Thornton |
| 6,575,159 B1 | 6/2003 | Frye et al. |
| 6,575,944 B1 | 6/2003 | McNary et al. |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,591,834 B1 | 7/2003 | Colla et al. |
| 6,591,835 B1 | 7/2003 | Blanch |
| 6,595,207 B1 | 7/2003 | McDonald et al. |
| 6,595,215 B2 | 7/2003 | Wood |
| 6,609,517 B1 | 8/2003 | Estes et al. |
| 6,622,726 B1 | 9/2003 | Du |
| 6,626,174 B1 | 9/2003 | Genger et al. |
| 6,626,175 B2 | 9/2003 | Jafari et al. |
| 6,629,525 B2 | 10/2003 | Hill et al. |

(56) References Cited

U.S. PATENT DOCUMENTS

| | | |
|---|---|---|
| 6,629,527 B1 | 10/2003 | Estes et al. |
| 6,629,529 B2 | 10/2003 | Arnott |
| 6,631,919 B1 | 10/2003 | West et al. |
| 6,634,356 B1 | 10/2003 | O'Dea et al. |
| 6,635,021 B1 | 10/2003 | Sullivan et al. |
| 6,640,806 B2 | 11/2003 | Yurko |
| 6,644,305 B2 | 11/2003 | MacRae et al. |
| 6,644,311 B1 | 11/2003 | Truitt et al. |
| 6,644,315 B2 | 11/2003 | Ziaee |
| 6,651,653 B1 | 11/2003 | Honkonen et al. |
| 6,651,656 B2 | 11/2003 | Demers et al. |
| 6,651,658 B1 | 11/2003 | Hill et al. |
| 6,655,382 B1 | 12/2003 | Kolobow |
| 6,655,385 B1 | 12/2003 | Curti et al. |
| 6,666,208 B1 | 12/2003 | Schumacher et al. |
| 6,668,828 B1 | 12/2003 | Figley et al. |
| 6,668,829 B2 | 12/2003 | Biondi et al. |
| 6,669,712 B1 | 12/2003 | Cardoso |
| 6,675,796 B2 | 1/2004 | McDonald |
| 6,675,801 B2 | 1/2004 | Wallace et al. |
| 6,679,265 B2 | 1/2004 | Strickland et al. |
| 6,681,764 B1 | 1/2004 | Honkonen et al. |
| 6,684,883 B1 | 2/2004 | Burns |
| 6,691,702 B2 | 2/2004 | Appel et al. |
| 6,691,707 B1 | 2/2004 | Gunaratnam et al. |
| 6,694,973 B1 | 2/2004 | Dunhao et al. |
| 6,694,978 B1 | 2/2004 | Bennarsten |
| 6,698,423 B1 | 3/2004 | Honkonen et al. |
| 6,705,314 B1 | 3/2004 | O'Dea |
| 6,705,315 B2 | 3/2004 | Sullivan et al. |
| 6,722,360 B2 | 4/2004 | Doshi |
| 6,722,362 B2 | 4/2004 | Hete et al. |
| 6,742,517 B1 | 6/2004 | Frye et al. |
| 6,745,768 B2 | 6/2004 | Colla et al. |
| 6,752,150 B1 | 6/2004 | Remmers et al. |
| 6,752,151 B2 | 6/2004 | Hill |
| 6,752,152 B2 | 6/2004 | Gale et al. |
| 6,755,193 B2 | 6/2004 | Berthon-Jones et al. |
| 6,758,217 B1 | 7/2004 | Younes |
| 6,761,172 B2 | 7/2004 | Boussignac et al. |
| 6,763,832 B1 | 7/2004 | Kirsch et al. |
| 6,769,432 B1 | 8/2004 | Keifer |
| 6,776,162 B2 | 8/2004 | Wood |
| 6,776,163 B2 | 8/2004 | Dougill et al. |
| 6,789,539 B2 | 9/2004 | Martinez |
| 6,796,305 B1 | 9/2004 | Banner et al. |
| 6,799,575 B1 | 10/2004 | Carter |
| 6,805,126 B2 | 10/2004 | Dutkiewicz |
| 6,807,966 B2 | 10/2004 | Wright |
| 6,807,967 B2 | 10/2004 | Wood |
| 6,810,876 B2 | 11/2004 | Berthon-Jones |
| 6,814,073 B2 | 11/2004 | Wickham |
| 6,814,077 B1 | 11/2004 | Eistert |
| 6,823,866 B2 | 11/2004 | Jafari et al. |
| 6,827,340 B2 | 12/2004 | Austin et al. |
| 6,837,238 B2 | 1/2005 | McDonald |
| 6,840,240 B1 | 1/2005 | Berthon-Jones et al. |
| 6,843,247 B2 | 1/2005 | Frye et al. |
| 6,848,446 B2 | 2/2005 | Noble |
| 6,854,462 B2 | 2/2005 | Berthon-Jones et al. |
| 6,863,069 B2 | 3/2005 | Wood |
| 6,866,041 B2 | 3/2005 | Hardy, Jr. et al. |
| 6,877,511 B2 | 4/2005 | DeVries et al. |
| 6,880,556 B2 | 4/2005 | Uchiyama et al. |
| 6,910,480 B1 | 6/2005 | Berthon-Jones |
| 6,910,482 B2 | 6/2005 | Bliss et al. |
| 6,910,510 B2 | 6/2005 | Gale et al. |
| 6,913,601 B2 | 7/2005 | St. Goar et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,938,620 B2 | 9/2005 | Payne, Jr. |
| 6,941,950 B2 | 9/2005 | Wilson et al. |
| 6,948,497 B2 | 9/2005 | Zdrojkowski et al. |
| 6,951,217 B2 | 10/2005 | Berthon-Jones |
| 6,971,382 B1 | 12/2005 | Corso |
| 6,986,353 B2 | 1/2006 | Wright |
| 6,994,089 B2 | 2/2006 | Wood |
| 6,997,177 B2 | 2/2006 | Wood |
| 6,997,881 B2 | 2/2006 | Green et al. |
| 7,000,612 B2 | 2/2006 | Jafari et al. |
| 7,004,170 B1 | 2/2006 | Gillstrom |
| 7,007,692 B2 | 3/2006 | Aylsworth et al. |
| 7,011,091 B2 | 3/2006 | Hill et al. |
| 7,013,892 B2 | 3/2006 | Estes et al. |
| 7,013,898 B2 | 3/2006 | Rashad et al. |
| 7,017,574 B2 | 3/2006 | Biondi et al. |
| 7,017,575 B2 | 3/2006 | Yagi et al. |
| 7,024,945 B2 | 4/2006 | Wallace |
| 7,036,504 B2 | 5/2006 | Wallace et al. |
| 7,044,129 B1 | 5/2006 | Truschel et al. |
| 7,047,969 B2 | 5/2006 | Noble |
| 7,047,974 B2 | 5/2006 | Strickland et al. |
| 7,051,735 B2 | 5/2006 | Mechlenburg et al. |
| 7,055,522 B2 | 6/2006 | Berthon-Jones |
| 7,059,328 B2 | 6/2006 | Wood |
| 7,066,173 B2 | 6/2006 | Banner et al. |
| 7,066,178 B2 | 6/2006 | Gunaratnam et al. |
| 7,077,132 B2 | 7/2006 | Berthon-Jones |
| 7,077,133 B2 | 7/2006 | Yagi et al. |
| 7,080,645 B2 | 7/2006 | Genger et al. |
| 7,080,646 B2 | 7/2006 | Wiesmann et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,121,277 B2 | 10/2006 | Strom |
| 7,128,578 B2 | 10/2006 | Lampotang et al. |
| 7,152,598 B2 | 12/2006 | Morris et al. |
| 7,152,604 B2 | 12/2006 | Hickle et al. |
| 7,156,090 B2 | 1/2007 | Nomori |
| 7,156,097 B2 | 1/2007 | Cardoso |
| 7,162,296 B2 | 1/2007 | Leonhardt et al. |
| 7,168,429 B2 | 1/2007 | Matthews et al. |
| 7,188,621 B2 | 3/2007 | DeVries et al. |
| 7,188,624 B2 | 3/2007 | Wood |
| 7,195,016 B2 | 3/2007 | Loyd et al. |
| 7,195,018 B1 | 3/2007 | Goldstein |
| 7,201,169 B2 | 4/2007 | Wilkie et al. |
| 7,201,269 B2 | 4/2007 | Buscher et al. |
| D542,912 S | 5/2007 | Gunaratnam et al. |
| 7,222,623 B2 | 5/2007 | DeVries et al. |
| 7,225,811 B2 | 6/2007 | Ruiz et al. |
| 7,234,465 B2 | 6/2007 | Wood |
| 7,237,205 B2 | 6/2007 | Sarel |
| 7,246,620 B2 | 7/2007 | Conroy, Jr. |
| D549,323 S | 8/2007 | Kwok et al. |
| 7,255,103 B2 | 8/2007 | Bassin |
| 7,255,107 B1 | 8/2007 | Gomez |
| 7,267,122 B2 | 9/2007 | Hill |
| 7,267,123 B2 | 9/2007 | Aylsworth et al. |
| 7,270,126 B2 | 9/2007 | Wallace et al. |
| 7,270,128 B2 | 9/2007 | Berthon-Jones et al. |
| 7,296,569 B2 | 11/2007 | Frye et al. |
| 7,296,573 B2 | 11/2007 | Estes et al. |
| D557,802 S | 12/2007 | Miceli, Jr. et al. |
| 7,302,950 B2 | 12/2007 | Berthon-Jones et al. |
| 7,305,987 B2 | 12/2007 | Scholler et al. |
| 7,318,437 B2 | 1/2008 | Gunaratnam et al. |
| 7,320,321 B2 | 1/2008 | Pranger et al. |
| 7,328,703 B1 | 2/2008 | Tiep |
| 7,353,826 B2 | 4/2008 | Sleeper et al. |
| 7,367,337 B2 | 5/2008 | Berthon-Jones et al. |
| 7,370,652 B2 | 5/2008 | Matula, Jr. et al. |
| 7,373,939 B1 | 5/2008 | DuBois et al. |
| 7,406,966 B2 | 8/2008 | Wondka |
| 7,418,965 B2 | 9/2008 | Fukunaga et al. |
| 7,422,015 B2 | 9/2008 | Delisle et al. |
| 7,431,035 B2 | 10/2008 | Mizuta et al. |
| 7,451,762 B2 | 11/2008 | Chua et al. |
| 7,455,717 B2 | 11/2008 | Sprinkle |
| 7,461,656 B2 | 12/2008 | Gunaratnam et al. |

(56) References Cited

U.S. PATENT DOCUMENTS

| | | |
|---|---|---|
| 7,468,040 B2 | 12/2008 | Hartley et al. |
| 7,469,697 B2 | 12/2008 | Lee et al. |
| 7,472,702 B2 | 1/2009 | Beck et al. |
| 7,478,641 B2 | 1/2009 | Rousselet |
| 7,481,219 B2 | 1/2009 | Lewis et al. |
| 7,481,221 B2 | 1/2009 | Kullik et al. |
| 7,487,774 B2 | 2/2009 | Acker |
| 7,487,778 B2 | 2/2009 | Freitag |
| 7,490,605 B2 | 2/2009 | Frye et al. |
| D588,258 S | 3/2009 | Judson et al. |
| D589,139 S | 3/2009 | Guney et al. |
| 7,500,482 B2 | 3/2009 | Biederman |
| 7,509,957 B2 | 3/2009 | Duquette et al. |
| D591,419 S | 4/2009 | Chandran et al. |
| 7,533,670 B1 | 5/2009 | Freitag et al. |
| 7,556,038 B2 | 7/2009 | Kirby et al. |
| 7,559,327 B2 | 7/2009 | Hernandez |
| 7,562,657 B2 | 7/2009 | Blanch et al. |
| 7,562,659 B2 | 7/2009 | Matarasso |
| 7,578,294 B2 | 8/2009 | Pierro et al. |
| 7,588,033 B2 | 9/2009 | Wondka |
| 7,591,265 B2 | 9/2009 | Lee et al. |
| 7,631,642 B2 | 12/2009 | Freitag et al. |
| 7,640,934 B2 | 1/2010 | Zollinger et al. |
| 7,658,189 B2 | 2/2010 | Davidson et al. |
| D614,288 S | 4/2010 | Judson et al. |
| 7,721,733 B2 | 5/2010 | Hughes et al. |
| 7,721,736 B2 | 5/2010 | Urias et al. |
| 7,740,013 B2 | 6/2010 | Ishizaki et al. |
| 7,743,770 B2 | 6/2010 | Curti et al. |
| 7,762,253 B2 | 7/2010 | Acker et al. |
| 7,766,009 B2 | 8/2010 | Frye et al. |
| 7,787,946 B2 | 8/2010 | Stahmann et al. |
| 7,814,906 B2 | 10/2010 | Moretti |
| 7,819,120 B2 | 10/2010 | Taylor et al. |
| D626,646 S | 11/2010 | Lubke et al. |
| D627,059 S | 11/2010 | Wood et al. |
| 7,832,400 B2 | 11/2010 | Curti et al. |
| 7,837,761 B2 | 11/2010 | Bliss et al. |
| 7,841,343 B2 | 11/2010 | Deane et al. |
| 7,845,350 B1 | 12/2010 | Kayyali et al. |
| 7,849,854 B2 | 12/2010 | DeVries et al. |
| 7,856,982 B2 | 12/2010 | Matula, Jr. et al. |
| 7,866,318 B2 | 1/2011 | Bassin |
| 7,874,290 B2 | 1/2011 | Chalvignac |
| 7,874,291 B2 | 1/2011 | Ging et al. |
| 7,874,293 B2 | 1/2011 | Gunaratnam et al. |
| 7,878,980 B2 | 2/2011 | Ricciardelli |
| 7,882,834 B2 | 2/2011 | Gradon et al. |
| 7,886,740 B2 | 2/2011 | Thomas et al. |
| 7,891,353 B2 | 2/2011 | Chalvignac |
| 7,891,357 B2 | 2/2011 | Carron et al. |
| 7,896,958 B2 | 3/2011 | Sermet et al. |
| 7,900,627 B2 | 3/2011 | Aylsworth et al. |
| 7,900,628 B2 | 3/2011 | Matula, Jr. et al. |
| 7,900,635 B2 | 3/2011 | Gunaratnam et al. |
| 7,901,361 B2 | 3/2011 | Rapoport et al. |
| 7,905,231 B2 | 3/2011 | Chalvignac |
| 7,913,691 B2 | 3/2011 | Farrugia |
| 7,914,459 B2 | 3/2011 | Green et al. |
| 7,918,226 B2 | 4/2011 | Acker et al. |
| 7,926,486 B2 | 4/2011 | Childers |
| 7,926,487 B2 | 4/2011 | Drew et al. |
| 7,931,023 B2 | 4/2011 | Berthon-Jones et al. |
| 7,934,499 B2 | 5/2011 | Berthon-Jones |
| 7,938,114 B2 | 5/2011 | Matthews et al. |
| 7,942,150 B2 | 5/2011 | Guney et al. |
| 7,942,380 B2 | 5/2011 | Bertinetti et al. |
| 7,958,892 B2 | 6/2011 | Kwok et al. |
| 7,975,694 B2 | 7/2011 | Ho |
| 7,980,245 B2 | 7/2011 | Rice et al. |
| 7,987,847 B2 | 8/2011 | Wickham et al. |
| 7,987,850 B2 | 8/2011 | Zollinger et al. |
| 7,987,851 B2 | 8/2011 | Blom et al. |
| 7,992,557 B2 | 8/2011 | Nadjafizadeh et al. |
| 7,997,270 B2 | 8/2011 | Meier |
| 7,997,271 B2 | 8/2011 | Hickle et al. |
| 7,997,272 B2 | 8/2011 | Isaza |
| 8,001,967 B2 | 8/2011 | Wallace et al. |
| D645,557 S | 9/2011 | Scheiner et al. |
| 8,011,365 B2 | 9/2011 | Douglas et al. |
| 8,011,366 B2 | 9/2011 | Knepper |
| 8,015,971 B2 | 9/2011 | Kwok |
| 8,015,974 B2 | 9/2011 | Christopher et al. |
| 8,020,558 B2 | 9/2011 | Christopher et al. |
| 8,025,052 B2 | 9/2011 | Matthews et al. |
| RE42,843 E | 10/2011 | Strickland et al. |
| 8,042,535 B2 | 10/2011 | Kenyon et al. |
| 8,042,537 B2 | 10/2011 | Mechlenburg et al. |
| 8,042,539 B2 | 10/2011 | Chandran et al. |
| 8,042,546 B2 | 10/2011 | Gunaratnam et al. |
| 8,061,354 B2 | 11/2011 | Schneider et al. |
| 8,066,004 B2 | 11/2011 | Morris et al. |
| 2001/0035185 A1 | 11/2001 | Christopher |
| 2001/0035186 A1 | 11/2001 | Hill |
| 2001/0042548 A1 | 11/2001 | Boussignac |
| 2002/0014238 A1* | 2/2002 | Kotmel ............... 128/204.18 |
| 2002/0014241 A1 | 2/2002 | Gradon et al. |
| 2002/0017300 A1 | 2/2002 | Hickle et al. |
| 2002/0020930 A1 | 2/2002 | Austin et al. |
| 2002/0026941 A1 | 3/2002 | Biondi et al. |
| 2002/0043264 A1 | 4/2002 | Wickham |
| 2002/0046751 A1 | 4/2002 | MacRae et al. |
| 2002/0046755 A1 | 4/2002 | De Voss |
| 2002/0046756 A1 | 4/2002 | Laizzo et al. |
| 2002/0053346 A1 | 5/2002 | Curti et al. |
| 2002/0055685 A1 | 5/2002 | Levitsky et al. |
| 2002/0059935 A1 | 5/2002 | Wood |
| 2002/0066452 A1 | 6/2002 | Kessler et al. |
| 2002/0078957 A1 | 6/2002 | Remmers et al. |
| 2002/0092527 A1 | 7/2002 | Wood |
| 2002/0112730 A1 | 8/2002 | Dutkiewicz |
| 2002/0153010 A1 | 10/2002 | Rozenberg et al. |
| 2002/0157673 A1 | 10/2002 | Kessler et al. |
| 2002/0159323 A1 | 10/2002 | Makabe et al. |
| 2002/0179090 A1 | 12/2002 | Boussignac |
| 2003/0000522 A1 | 1/2003 | Lynn et al. |
| 2003/0047185 A1 | 3/2003 | Olsen et al. |
| 2003/0069489 A1 | 4/2003 | Abreu |
| 2003/0079749 A1 | 5/2003 | Strickland et al. |
| 2003/0094178 A1 | 5/2003 | McAuley et al. |
| 2003/0111081 A1 | 6/2003 | Gupta |
| 2003/0116163 A1 | 6/2003 | Wood |
| 2003/0121519 A1 | 7/2003 | Estes et al. |
| 2003/0145852 A1 | 8/2003 | Schmidt et al. |
| 2003/0145853 A1 | 8/2003 | Muellner |
| 2003/0145856 A1 | 8/2003 | Zdrojkowski et al. |
| 2003/0150455 A1 | 8/2003 | Bliss et al. |
| 2003/0159696 A1 | 8/2003 | Boussignac et al. |
| 2003/0159697 A1 | 8/2003 | Wallace |
| 2003/0168067 A1 | 9/2003 | Dougill et al. |
| 2003/0213488 A1 | 11/2003 | Remmers et al. |
| 2003/0221687 A1 | 12/2003 | Kaigler |
| 2003/0230308 A1 | 12/2003 | Linden |
| 2004/0020493 A1 | 2/2004 | Wood |
| 2004/0025881 A1 | 2/2004 | Gunaratnam et al. |
| 2004/0035431 A1 | 2/2004 | Wright |
| 2004/0040560 A1 | 3/2004 | Euliano et al. |
| 2004/0050387 A1 | 3/2004 | Younes |
| 2004/0074494 A1 | 4/2004 | Frater |
| 2004/0159323 A1 | 8/2004 | Schmidt et al. |
| 2004/0206352 A1 | 10/2004 | Conroy |
| 2004/0221848 A1 | 11/2004 | Hill |
| 2004/0221854 A1 | 11/2004 | Hete et al. |
| 2004/0226566 A1 | 11/2004 | Gunaratnam et al. |
| 2004/0231674 A1 | 11/2004 | Tanaka |
| 2004/0237963 A1 | 12/2004 | Berthon-Jones |
| 2004/0254501 A1 | 12/2004 | Mault |
| 2004/0255943 A1 | 12/2004 | Morris et al. |
| 2005/0005938 A1 | 1/2005 | Berthon-Jones et al. |
| 2005/0010125 A1 | 1/2005 | Joy et al. |
| 2005/0011524 A1 | 1/2005 | Thomlinson et al. |
| 2005/0016534 A1 | 1/2005 | Ost |
| 2005/0033247 A1 | 2/2005 | Thompson |

(56) References Cited

U.S. PATENT DOCUMENTS

| | | |
|---|---|---|
| 2005/0034724 A1 | 2/2005 | O'Dea |
| 2005/0061322 A1 | 3/2005 | Freitag |
| 2005/0061326 A1 | 3/2005 | Payne |
| 2005/0072430 A1 | 4/2005 | Djupesland |
| 2005/0081849 A1 | 4/2005 | Warren |
| 2005/0087190 A1 | 4/2005 | Jafari et al. |
| 2005/0098179 A1 | 5/2005 | Burton et al. |
| 2005/0103343 A1 | 5/2005 | Gosweiler |
| 2005/0121033 A1 | 6/2005 | Starr et al. |
| 2005/0121037 A1 | 6/2005 | Wood |
| 2005/0121038 A1 | 6/2005 | Christopher |
| 2005/0150498 A1 | 7/2005 | McDonald |
| 2005/0161049 A1 | 7/2005 | Wright |
| 2005/0166924 A1 | 8/2005 | Thomas et al. |
| 2005/0199242 A1 | 9/2005 | Matula et al. |
| 2005/0205096 A1 | 9/2005 | Matula et al. |
| 2005/0247308 A1 | 11/2005 | Frye et al. |
| 2005/0257793 A1 | 11/2005 | Tatsumoto |
| 2005/0274381 A1 | 12/2005 | Deane et al. |
| 2006/0005834 A1 | 1/2006 | Aylsworth et al. |
| 2006/0005842 A1 | 1/2006 | Rashad et al. |
| 2006/0011199 A1 | 1/2006 | Rashad et al. |
| 2006/0027234 A1 | 2/2006 | Gradon et al. |
| 2006/0048781 A1 | 3/2006 | Nawata |
| 2006/0054169 A1 | 3/2006 | Han et al. |
| 2006/0070625 A1 | 4/2006 | Ayappa et al. |
| 2006/0079799 A1 | 4/2006 | Green et al. |
| 2006/0096596 A1 | 5/2006 | Occhialini et al. |
| 2006/0107958 A1 | 5/2006 | Sleeper |
| 2006/0112959 A1 | 6/2006 | Mechlenburg et al. |
| 2006/0124131 A1 | 6/2006 | Chandran et al. |
| 2006/0124134 A1 | 6/2006 | Wood |
| 2006/0137690 A1 | 6/2006 | Gunaratnam et al. |
| 2006/0144396 A1 | 7/2006 | DeVries et al. |
| 2006/0149144 A1 | 7/2006 | Lynn et al. |
| 2006/0150972 A1 | 7/2006 | Mizuta et al. |
| 2006/0150973 A1 | 7/2006 | Chalvignac |
| 2006/0150982 A1 | 7/2006 | Wood |
| 2006/0151624 A1 | 7/2006 | Grundler et al. |
| 2006/0174877 A1 | 8/2006 | Jagger et al. |
| 2006/0180149 A1 | 8/2006 | Matarasso |
| 2006/0185669 A1 | 8/2006 | Bassovitch |
| 2006/0201504 A1 | 9/2006 | Singhal et al. |
| 2006/0213518 A1 | 9/2006 | DeVries et al. |
| 2006/0213519 A1 | 9/2006 | Schmidt et al. |
| 2006/0225737 A1 | 10/2006 | Iobbi |
| 2006/0237013 A1 | 10/2006 | Kwok |
| 2006/0243278 A1 | 11/2006 | Hamilton et al. |
| 2006/0249155 A1 | 11/2006 | Gambone |
| 2006/0266361 A1 | 11/2006 | Hernandez |
| 2007/0000490 A1 | 1/2007 | DeVries et al. |
| 2007/0000495 A1 | 1/2007 | Matula et al. |
| 2007/0017515 A1 | 1/2007 | Wallace et al. |
| 2007/0056590 A1 | 3/2007 | Wolfson |
| 2007/0062529 A1 | 3/2007 | Choncholas et al. |
| 2007/0068528 A1 | 3/2007 | Bohm et al. |
| 2007/0074724 A1 | 4/2007 | Duquette et al. |
| 2007/0089743 A1 | 4/2007 | Hoffman |
| 2007/0089745 A1 | 4/2007 | Gabriel et al. |
| 2007/0095347 A1 | 5/2007 | Lampotang et al. |
| 2007/0107728 A1 | 5/2007 | Ricciardelli et al. |
| 2007/0107732 A1 | 5/2007 | Dennis et al. |
| 2007/0107737 A1 | 5/2007 | Landis et al. |
| 2007/0113850 A1 | 5/2007 | Acker et al. |
| 2007/0113856 A1 | 5/2007 | Acker et al. |
| 2007/0125379 A1 | 6/2007 | Pierro et al. |
| 2007/0137653 A1 | 6/2007 | Wood |
| 2007/0163600 A1 | 7/2007 | Hoffman |
| 2007/0173705 A1 | 7/2007 | Teller et al. |
| 2007/0181125 A1 | 8/2007 | Mulier |
| 2007/0193705 A1 | 8/2007 | Hsu |
| 2007/0199568 A1 | 8/2007 | Diekens et al. |
| 2007/0209662 A1 | 9/2007 | Bowen et al. |
| 2007/0215156 A1 | 9/2007 | Kwok |
| 2007/0232950 A1 | 10/2007 | West |
| 2007/0240716 A1 | 10/2007 | Marx |
| 2007/0251528 A1 | 11/2007 | Seitz et al. |
| 2007/0272249 A1 | 11/2007 | Chandran et al. |
| 2008/0000475 A1 | 1/2008 | Hill |
| 2008/0006271 A1 | 1/2008 | Aylsworth et al. |
| 2008/0011298 A1 | 1/2008 | Mazar et al. |
| 2008/0011301 A1 | 1/2008 | Qian |
| 2008/0041371 A1 | 2/2008 | Freitag |
| 2008/0041386 A1 | 2/2008 | Dodier et al. |
| 2008/0045815 A1 | 2/2008 | Derchak et al. |
| 2008/0047559 A1 | 2/2008 | Fiori |
| 2008/0051674 A1 | 2/2008 | Davenport et al. |
| 2008/0053438 A1 | 3/2008 | DeVries et al. |
| 2008/0053447 A1 | 3/2008 | Ratajczak et al. |
| 2008/0060646 A1 | 3/2008 | Isaza |
| 2008/0060657 A1 | 3/2008 | McAuley et al. |
| 2008/0066753 A1 | 3/2008 | Martin et al. |
| 2008/0072902 A1 | 3/2008 | Setzer et al. |
| 2008/0078392 A1 | 4/2008 | Pelletier et al. |
| 2008/0078407 A1 | 4/2008 | Sherman |
| 2008/0092904 A1 | 4/2008 | Gunarathnam et al. |
| 2008/0092905 A1 | 4/2008 | Gunarathnam et al. |
| 2008/0092906 A1 | 4/2008 | Gunarathnam et al. |
| 2008/0099024 A1 | 5/2008 | Gunarathnam et al. |
| 2008/0099027 A1 | 5/2008 | Gunaratnam et al. |
| 2008/0105264 A1 | 5/2008 | Gunarathnam et al. |
| 2008/0110462 A1 | 5/2008 | Chekal et al. |
| 2008/0121230 A1 | 5/2008 | Cortez et al. |
| 2008/0134690 A1 | 6/2008 | Reid |
| 2008/0135044 A1 | 6/2008 | Freitag et al. |
| 2008/0142013 A1 | 6/2008 | Hallett et al. |
| 2008/0142019 A1 | 6/2008 | Lewis et al. |
| 2008/0161653 A1 | 7/2008 | Lin et al. |
| 2008/0173304 A1 | 7/2008 | Zaiser et al. |
| 2008/0178880 A1 | 7/2008 | Christopher et al. |
| 2008/0178881 A1 | 7/2008 | Whitcher et al. |
| 2008/0178882 A1 | 7/2008 | Christopher et al. |
| 2008/0185002 A1 | 8/2008 | Berthon-Jones et al. |
| 2008/0185007 A1 | 8/2008 | Sleeper et al. |
| 2008/0190429 A1 | 8/2008 | Tatarek |
| 2008/0190436 A1 | 8/2008 | Jaffe et al. |
| 2008/0196715 A1 | 8/2008 | Yamamori |
| 2008/0196723 A1 | 8/2008 | Tilley |
| 2008/0196728 A1 | 8/2008 | Ho |
| 2008/0202528 A1 | 8/2008 | Carter et al. |
| 2008/0216834 A1 | 9/2008 | Easley et al. |
| 2008/0216838 A1 | 9/2008 | Wondka |
| 2008/0216841 A1 | 9/2008 | Grimes et al. |
| 2008/0223369 A1 | 9/2008 | Warren |
| 2008/0245369 A1 | 10/2008 | Matula et al. |
| 2008/0251079 A1 | 10/2008 | Richey |
| 2008/0264417 A1 | 10/2008 | Manigel et al. |
| 2008/0283060 A1 | 11/2008 | Bassin |
| 2008/0295846 A1 | 12/2008 | Han et al. |
| 2008/0302364 A1 | 12/2008 | Garde et al. |
| 2008/0308104 A1 | 12/2008 | Blomberg et al. |
| 2009/0007911 A1 | 1/2009 | Cleary et al. |
| 2009/0020015 A1 | 1/2009 | Sermet et al. |
| 2009/0020121 A1 | 1/2009 | Bassin |
| 2009/0044808 A1 | 2/2009 | Guney et al. |
| 2009/0056708 A1 | 3/2009 | Stenzler et al. |
| 2009/0078255 A1 | 3/2009 | Bowman et al. |
| 2009/0078258 A1 | 3/2009 | Bowman et al. |
| 2009/0095298 A1 | 4/2009 | Gunaratnam et al. |
| 2009/0095300 A1 | 4/2009 | McMorrow |
| 2009/0095303 A1 | 4/2009 | Sher et al. |
| 2009/0099471 A1 | 4/2009 | Broadley et al. |
| 2009/0101147 A1 | 4/2009 | Landis et al. |
| 2009/0101154 A1 | 4/2009 | Mutti et al. |
| 2009/0107502 A1 | 4/2009 | Younes |
| 2009/0118632 A1 | 5/2009 | Goepp |
| 2009/0120437 A1 | 5/2009 | Oates et al. |
| 2009/0126739 A1 | 5/2009 | Ng et al. |
| 2009/0133699 A1 | 5/2009 | Nalagatla et al. |
| 2009/0139527 A1 | 6/2009 | Ng et al. |
| 2009/0145435 A1 | 6/2009 | White et al. |
| 2009/0151719 A1 | 6/2009 | Wondka et al. |
| 2009/0151724 A1 | 6/2009 | Wondka et al. |
| 2009/0151726 A1 | 6/2009 | Freitag |

(56) References Cited

U.S. PATENT DOCUMENTS

| | | |
|---|---|---|
| 2009/0151729 A1 | 6/2009 | Judson et al. |
| 2009/0156953 A1 | 6/2009 | Wondka et al. |
| 2009/0165799 A1 | 7/2009 | Duquette et al. |
| 2009/0173347 A1 | 7/2009 | Berthon-Jones |
| 2009/0173349 A1 | 7/2009 | Hernandez et al. |
| 2009/0183739 A1 | 7/2009 | Wondka |
| 2009/0199855 A1 | 8/2009 | Davenport |
| 2009/0205662 A1 | 8/2009 | Kwok et al. |
| 2009/0235880 A1 | 9/2009 | Ziegs |
| 2009/0241947 A1 | 10/2009 | Bedini et al. |
| 2009/0241951 A1 | 10/2009 | Jafari et al. |
| 2009/0250066 A1 | 10/2009 | Daly |
| 2009/0255533 A1 | 10/2009 | Freitag et al. |
| 2009/0260625 A1 | 10/2009 | Wondka |
| 2009/0277452 A1 | 11/2009 | Lubke et al. |
| 2009/0293877 A1 | 12/2009 | Blanch et al. |
| 2009/0301495 A1 | 12/2009 | Pierro et al. |
| 2009/0308395 A1 | 12/2009 | Lee et al. |
| 2009/0320851 A1 | 12/2009 | Selvarajan et al. |
| 2010/0018534 A1 | 1/2010 | Veliss et al. |
| 2010/0043786 A1 | 2/2010 | Freitag et al. |
| 2010/0071693 A1 | 3/2010 | Allum et al. |
| 2010/0071697 A1 | 3/2010 | Jafari et al. |
| 2010/0083968 A1 | 4/2010 | Wondka et al. |
| 2010/0108073 A1 | 5/2010 | Zollinger et al. |
| 2010/0132716 A1 | 6/2010 | Selvarajan et al. |
| 2010/0132717 A1 | 6/2010 | Davidson et al. |
| 2010/0163043 A1 | 7/2010 | Hart et al. |
| 2010/0170512 A1 | 7/2010 | Kuypers et al. |
| 2010/0170513 A1 | 7/2010 | Bowditch et al. |
| 2010/0192957 A1 | 8/2010 | Hobson et al. |
| 2010/0218766 A1 | 9/2010 | Milne |
| 2010/0224196 A1 | 9/2010 | Jablons |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0252044 A1 | 10/2010 | Duquette et al. |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282251 A1 | 11/2010 | Calluaud et al. |
| 2010/0282810 A1 | 11/2010 | Hawes |
| 2010/0288279 A1 | 11/2010 | Seiver et al. |
| 2010/0288289 A1 | 11/2010 | Nasir |
| 2010/0300445 A1 | 12/2010 | Chatburn et al. |
| 2010/0300446 A1 | 12/2010 | Nicolazzi et al. |
| 2010/0307487 A1 | 12/2010 | Dunsmore et al. |
| 2010/0307495 A1 | 12/2010 | Kepler et al. |
| 2010/0307499 A1 | 12/2010 | Eger et al. |
| 2010/0307500 A1 | 12/2010 | Armitstead |
| 2010/0307502 A1 | 12/2010 | Rummery et al. |
| 2010/0313891 A1 | 12/2010 | Veliss et al. |
| 2010/0313898 A1 | 12/2010 | Richard et al. |
| 2010/0319703 A1 | 12/2010 | Hayman et al. |
| 2010/0326441 A1 | 12/2010 | Zucker et al. |
| 2010/0326446 A1 | 12/2010 | Behlmaier |
| 2011/0000489 A1 | 1/2011 | Laksov et al. |
| 2011/0009763 A1 | 1/2011 | Levitsky et al. |
| 2011/0011402 A1 | 1/2011 | Berthon-Jones |
| 2011/0023878 A1 | 2/2011 | Thiessen |
| 2011/0023881 A1 | 2/2011 | Thiessen |
| 2011/0034819 A1 | 2/2011 | Desforges et al. |
| 2011/0036352 A1 | 2/2011 | Estes et al. |
| 2011/0041850 A1 | 2/2011 | Vandine et al. |
| 2011/0041855 A1 | 2/2011 | Gunaratnam et al. |
| 2011/0061647 A1 | 3/2011 | Stahmann et al. |
| 2011/0067704 A1 | 3/2011 | Kooij et al. |
| 2011/0067709 A1 | 3/2011 | Doshi et al. |
| 2011/0071444 A1 | 3/2011 | Kassatly et al. |
| 2011/0073107 A1 | 3/2011 | Rodman et al. |
| 2011/0073116 A1 | 3/2011 | Genger et al. |
| 2011/0087123 A9 | 4/2011 | Choncholas et al. |
| 2011/0088690 A1 | 4/2011 | Djupesland et al. |
| 2011/0094518 A1 | 4/2011 | Cipollone et al. |
| 2011/0100365 A1 | 5/2011 | Wedler et al. |
| 2011/0114098 A1 | 5/2011 | McAuley et al. |
| 2011/0125052 A1 | 5/2011 | Davenport et al. |
| 2011/0126841 A1 | 6/2011 | Matula, Jr. et al. |
| 2011/0132363 A1 | 6/2011 | Chalvignac |
| 2011/0139153 A1 | 6/2011 | Chalvignac |
| 2011/0146687 A1 | 6/2011 | Fukushima |
| 2011/0155140 A1 | 6/2011 | Ho et al. |
| 2011/0162650 A1 | 7/2011 | Miller et al. |
| 2011/0162655 A1 | 7/2011 | Gunaratnam et al. |
| 2011/0178419 A1 | 7/2011 | Wood et al. |
| 2011/0180068 A1 | 7/2011 | Kenyon et al. |
| 2011/0197885 A1 | 8/2011 | Wondka et al. |
| 2011/0209705 A1 | 9/2011 | Freitag |
| 2011/0214676 A1 | 9/2011 | Allum et al. |
| 2011/0220105 A1 | 9/2011 | Meier |
| 2011/0232642 A1 | 9/2011 | Bliss et al. |
| 2011/0247625 A1 | 10/2011 | Boussignac |
| 2011/0253147 A1 | 10/2011 | Gusky et al. |
| 2011/0259327 A1 | 10/2011 | Wondka et al. |
| 2011/0265796 A1 | 11/2011 | Amarasinghe et al. |
| 2011/0277765 A1 | 11/2011 | Christopher et al. |
| 2011/0284003 A1 | 11/2011 | Douglas et al. |

FOREIGN PATENT DOCUMENTS

| | | |
|---|---|---|
| DE | 29902267 U1 | 7/1999 |
| DE | 19841070 | 5/2000 |
| DE | 19849571 | 5/2000 |
| DE | 10337138.9 | 3/2005 |
| DE | 10 2006 023 637.8 | 11/2007 |
| EP | 0125424 | 11/1984 |
| EP | 0692273 | 1/1996 |
| EP | 0778035 | 6/1997 |
| EP | 1359961 | 11/2003 |
| EP | 2377462 | 11/2010 |
| GB | 2174609 | 11/1986 |
| GB | 2201098 | 8/1988 |
| GB | 1055148 | 6/1989 |
| GB | 2338420 | 12/1999 |
| JP | S63-57060 | 3/1998 |
| JP | 2002-204830 | 7/2002 |
| WO | WO-92/11054 | 7/1992 |
| WO | WO-98/01176 | 1/1998 |
| WO | WO-99/04841 | 2/1999 |
| WO | WO-00/64521 | 11/2000 |
| WO | WO-01/76655 | 10/2001 |
| WO | WO-02/062413 | 8/2002 |
| WO | WO-2004/009169 | 1/2004 |
| WO | WO-2005/014091 | 2/2005 |
| WO | WO-2005/018524 | 3/2005 |
| WO | WO-2005/086943 | 9/2005 |
| WO | WO-2006/138580 | 12/2006 |
| WO | WO-2007/035804 | 3/2007 |
| WO | WO-2007/139531 | 12/2007 |
| WO | WO-2007142812 | 12/2007 |
| WO | WO-2008/014543 | 2/2008 |
| WO | WO-2008/019102 | 2/2008 |
| WO | WO-2008/052534 | 5/2008 |
| WO | WO-2008/112474 | 9/2008 |
| WO | WO-2008/138040 | 11/2008 |
| WO | WO-2008/144589 | 11/2008 |
| WO | WO-2008/144669 | 11/2008 |
| WO | WO-2009/042973 | 4/2009 |
| WO | WO-2009/042974 | 4/2009 |
| WO | WO-2009/059353 | 5/2009 |
| WO | WO-2009/064202 | 5/2009 |
| WO | WO-2009/074160 | 6/2009 |
| WO | WO-2009/082295 | 7/2009 |
| WO | WO-2009/087607 | 7/2009 |
| WO | WO-2009/092057 | 7/2009 |
| WO | WO-2009/103288 | 8/2009 |
| WO | WO-2009/109005 | 9/2009 |
| WO | WO-2009/115944 | 9/2009 |
| WO | WO-2009/115948 | 9/2009 |
| WO | WO-2009/115949 | 9/2009 |
| WO | WO-2009/129506 | 10/2009 |

(56) References Cited

FOREIGN PATENT DOCUMENTS

| WO | WO-2009/136101 | 11/2009 |
|---|---|---|
| WO | WO-2009/139647 | 11/2009 |
| WO | WO-2009/149351 | 12/2009 |
| WO | WO-2009/149353 | 12/2009 |
| WO | WO-2009/149355 | 12/2009 |
| WO | WO-2009/149357 | 12/2009 |
| WO | WO-2009/151344 | 12/2009 |
| WO | WO-2009/151791 | 12/2009 |
| WO | WO-2010/000135 | 1/2010 |
| WO | WO-2010/021556 | 2/2010 |
| WO | WO 2010/022363 | 2/2010 |
| WO | WO-2010/039989 | 4/2010 |
| WO | WO-2010/041966 | 4/2010 |
| WO | WO-2010/044034 | 4/2010 |
| WO | WO-2010/057268 | 5/2010 |
| WO | WO-2010/059049 | 5/2010 |
| WO | WO-2010/060422 | 6/2010 |
| WO | WO-2010/068356 | 6/2010 |
| WO | WO-2010/070493 | 6/2010 |
| WO | WO-2010/070497 | 6/2010 |
| WO | WO-2010/070498 | 6/2010 |
| WO | WO-2010/076711 | 7/2010 |
| WO | WO-2010/081223 | 7/2010 |
| WO | WO-2010/091157 | 8/2010 |
| WO | WO-2010/099375 | 9/2010 |
| WO | WO-2010/102094 | 9/2010 |
| WO | WO-2010/115166 | 10/2010 |
| WO | WO-2010/115168 | 10/2010 |
| WO | WO-2010/115169 | 10/2010 |
| WO | WO-2010/115170 | 10/2010 |
| WO | WO-2010/116275 | 10/2010 |
| WO | WO-2010/132853 | 11/2010 |
| WO | WO-2010/136923 | 12/2010 |
| WO | WO-2010/139014 | 12/2010 |
| WO | WO-2010/150187 | 12/2010 |
| WO | WO-2011/002608 | 1/2011 |
| WO | WO-2011/004274 | 1/2011 |
| WO | WO-2011/006184 | 1/2011 |
| WO | WO-2011/006199 | 1/2011 |
| WO | WO-2011/014931 | 2/2011 |
| WO | WO-2011/017033 | 2/2011 |
| WO | WO-2011/017738 | 2/2011 |
| WO | WO-2011/021978 | 2/2011 |
| WO | WO-2011/022779 | 3/2011 |
| WO | WO-2011/024383 | 3/2011 |
| WO | WO-2011/029073 | 3/2011 |
| WO | WO-2011/029074 | 3/2011 |
| WO | WO-2011/035373 | 3/2011 |
| WO | WO-2011/038950 | 4/2011 |
| WO | WO-2011/038951 | 4/2011 |
| WO | WO-2011/044627 | 4/2011 |
| WO | WO-2011/057362 | 5/2011 |
| WO | WO-2011/059346 | 5/2011 |
| WO | WO-2011/061648 | 5/2011 |
| WO | WO-2011/062510 | 5/2011 |
| WO | WO-2011/086437 | 7/2011 |
| WO | WO-2011/086438 | 7/2011 |
| WO | WO-2011/112807 | 9/2011 |

OTHER PUBLICATIONS

In the U.S. Patent and Trademark Office, Supplemental Notice of Allowance dated in re: U.S. Appl. No. 10/771,803, dated Nov. 7, 2008, 2 pages.
In the U.S. Patent and Trademark Office, Examiner's Interview Summary in re: U.S. Appl. No. 10/771,803, dated Oct. 31, 2008, 4 pages.
In the U.S. Patent and Trademark Office, Notice of Allowance dated in re: U.S. Appl. No. 10/771,803, dated Oct. 20, 2008, 8 pages.
In the U.S. Patent and Trademark Office, Examiner's Interview Summary in re: U.S. Appl. No. 10/771,803, dated Nov. 2, 2007, 2 pages.
In the U.S. Patent and Trademark Office, Office Action in re: U.S. Appl. No. 10/771,803, dated Jun. 14, 2007, 12 pages.
In the U.S. Patent and Trademark Office, Restriction Requirement in re: U.S. Appl. No. 12/271,484, dated Feb. 9, 2011, 5 pages.
In the U.S. Patent and Trademark Office, Restriction Requirement in re: U.S. Appl. No. 12/754,437, dated Aug. 16, 2011, 5 pages.
In the U.S. Patent and Trademark Office, Non-Final Office Action dated in re: U.S. Appl. No. 10/567,746, dated Oct. 5, 2009, 9 pages.
In the U.S. Patent and Trademark Office, Notice of Allowance and Examiner's Interview Summary in re: U.S. Appl. No. 11/523,519, dated Jan. 16, 2009, 10 pages.
In the U.S. Patent and Trademark Office, Examiner's Interview Summary in re: U.S. Appl. No. 11/523,519, dated Jan. 13, 2009, 4 pages.
In the U.S. Patent and Trademark Office, Final Office Action in re: U.S. Appl. No. 11/523,519, dated Jul. 11, 2008, 13 pages.
In the U.S. Patent and Trademark Office, Examiner's Interview Summary in re: U.S. Appl. No. 11/523,519, dated Apr. 10, 2008, 3 pages.
In the U.S. Patent and Trademark Office, Final Office Action in re: U.S. Appl. No. 11/523,519, dated Nov. 26, 2007, 14 pages.
In the U.S. Patent and Trademark Office, Office Action in re: U.S. Appl. No. 11/523,519, dated Mar. 7, 2007, 11 pages.
In the U.S. Patent and Trademark Office, Restriction Requirement in re: U.S. Appl. No. 11/523,518, dated Dec. 30, 2009, 4 pages.
In the U.S. Patent and Trademark Office, Supplemental Notice of Allowance in re: U.S. Appl. No. 11/798,965, dated Aug. 21, 2009, 4 pages.
In the U.S. Patent and Trademark Office, Notice of Allowance in re: U.S. Appl. No. 11/798,965, dated Jul. 17, 2009, 5 pages.
In the U.S. Patent and Trademark Office, Final Office Action in re: U.S. Appl. No. 11/798,965, dated Apr. 9, 2009, 6 pages.
In the U.S. Patent and Trademark Office, Office Action in re: U.S. Appl. No. 11/798,965, dated Jul. 29, 2008, 12 pages.
In the U.S. Patent and Trademark Office, Office Action in re: U.S. Appl. No. 12/578,283, dated Oct. 19, 2011, 5 pages.
In the U.S. Patent and Trademark Office, Restriction/Election Requirement in re: U.S. Appl. No. 11/882,530, dated Apr. 27, 2011, 5 pages.
In the U.S. Patent and Trademark Office, Supplemental Notice of Allowance in re: U.S. Appl. No. 10/870,849, dated Jun. 16, 2009, 2 pages.
In the U.S. Patent and Trademark Office, Notice of Allowance in re: U.S. Appl. No. 10/870,849, dated Jun. 3, 2009, 4 pages.
In the U.S. Patent and Trademark Office, Notice of Allowance in re: U.S. Appl. No. 10/870,849, dated May 14, 2009, 8 pages.
In the U.S. Patent and Trademark Office, Restriction in re: U.S. Appl. No. 10/870,849, dated Nov. 16, 2007, 5 pages.
In the U.S. Patent and Trademark Office, Examiner's Interview Summary in re: U.S. Appl. No. 10/870,849, dated Jul. 27, 2007, 2 pages.
In the U.S. Patent and Trademark Office, Office Action in re: U.S. Appl. No. 10/870,849, dated Feb. 22, 2007, 13 pages.
In the U.S. Patent and Trademark Office, Restriction/Election Requirement in re: U.S. Appl. No. 12/153,423, dated Oct. 6, 2011, 8 pages.
In the U.S. Patent and Trademark Office, Notice of Allowance in re: U.S. Appl. No. 10/922,054, dated Feb. 12, 2008, 6 pages.
In the U.S. Patent and Trademark Office, Final Office Action in re: U.S. Appl. No. 10/922,054, dated Nov. 27, 2007, 9 pages.
In the U.S. Patent and Trademark Office, Office Action in re: U.S. Appl. No. 10/922,054, dated Mar. 14, 2007, 14 pages.
In the U.S. Patent and Trademark Office, Office Action in re: U.S. Appl. No. 10/922,054, dated Sep. 7, 2006, 21 pages.
In the U.S. Patent and Trademark Office, Restriction Requirement in re: U.S. Appl. No. 10/922,054, dated May 17, 2006, 5 pages.
In the U.S. Patent and Trademark Office, Notice of Allowance and Examiner's Interview Summary in re: U.S. Appl. No. 12/076,062, dated Nov. 2, 2011, 8 pages.
In the U.S. Patent and Trademark Office, Office Action in re: U.S. Appl. No. 12/076,062, dated Jan. 13, 2011, 14 pages.
In the U.S. Patent and Trademark Office, Office Action in re: U.S. Appl. No. 12/355,753, dated Sep. 28, 2011, 32 pages.
In the U.S. Patent and Trademark Office, *Ex Parte Quayle* Office Action in re: U.S. Appl. No. 29/388,700, dated Oct. 7, 2011, 5 pages.
"AARC Clinical Practice Guideline: Oxygen Therapy in the Home or Extended Care Facility," *Resp. Care*, 1992: 37(8), pp. 918-922.
"ATS Statement: Guidelines for the Six-Minute Walk Test," *Am. J. Respir. Crit. Care Med.*, 2002: 166, pp. 111-117.
"Passy-Muir Speaking Valves," *Respiratory*, Nov. 13, 1998, 7 pages.

(56) References Cited

OTHER PUBLICATIONS

Ambrosino, "Exercise and noninvasive ventilatory support," *Monaldi Arch Chest Dis.*, 2000: 55(3): 242-246.
Ambrosino, "Weaning and Respiratory Muscle Dysfunction: The Egg Chicken Dilemma," Chest, 2005: 128(2), pp. 481-483.
Bach et al., "Intermittent Positive Pressure Ventilation via Nasal Access in the Management of Respiratory Insufficiency," *Chest*, 1987: 92(1), pp. 168-170.
Banner et al., "Extubating at a Pressure Support Ventilation Level Corresponding to Zero Imposed Work of Breathing," *Anesthesiology*, Sep. 1994: 81(3A), p. A271.
Banner et al., "Imposed Work of Breathing and Methods of Triggering a Demand-Flow, Continuous Positive Airway Pressure System," *Critical Care Medicine*, 1993: 21(2), pp. 183-190.
Banner et al., "Site of Pressure Measurement During Spontaneous Breathing with Continuous Positive Airway Pressure: Effect on Calculating Imposed Work of Breathing," *Critical Care Medicine*, 1992: 20(4), pp. 528-533.
Barakat et al., "Effect of noninvasive ventilatory support during exercise of a program in pulmonary rehabilitation in patients with COPD," *Int. J. Chron. Obstruct. Pulmon. Dis.*, 2007: 2(4), pp. 585-591.
Barreiro et al., "Noninvasive ventilation," *Crit Care Clin.*, 2007; 23(2): 201-22.
Bauer et al., "ADAM Nasal CPAP Circuit Adaptation: A Case Report," *Sleep*, 1991: 14(3), pp. 272-273.
Blanch, "Clinical Studies of Tracheal Gas Insufflation," *Resp. Care*, 2001: 45(2), pp. 158-166.
Borghi-Silva et al., "Non-invasive ventilation improves peripheral oxygen saturation and reduces fatigability of quadriceps in patients with COPD," Respirology, 2009, 14:537-546.
Bossi et al., "Continuous Positive Airway Pressure in the Spontaneously Breathing Newborn by Means of Bilateral Nasal Cannulation," *Monatsschr Kinderheilkd*, 1975: 123(4), pp. 141-146.
Boussarsar et al., "Relationship between ventilatory settings and barotrauma in the acute respiratory distress syndrome," Intensive Care Med., 2002: 28(4): 406-13.
Chang et al., "Reduced Inspiratory Muscle Endurance Following Successful Weaning From Prolonged Mechanical Ventilation," *Chest*, 2005: 128(2), pp. 553-559.
Charlotte Regional Medical Center, "Application of the Passy-Muir Tracheostomy and Ventilator," *Speech-Language Pathology Department*, Jan. 1995, 8 pages.
Christopher et al., "Preliminary Observations of Transtracheal Augmented Ventilation for Chronic Severe Respiratory Disease," *Resp. Care*, 2001: 46(1), pp. 15-25.
Christopher, et al., "Transtracheal Oxygen Therapy for Refractory Hypoxemia," *JAMA*, 1986: 256(4), pp. 494-497.
Ciccolella et al.; "Administration of High-Flow, Vapor-phased, Humidified Nasal Cannula Air (HF-HNC) Decreases Work of Breathing (WOB) in Healthy Subjects During Exercise," *AmJRCCM*, Apr. 2001: 163(5), Part 2, pp. A622. (Abstract Only).
Clini et al., "The Italian multicentre study on noninvasive ventilation in chronic obstructive pulmonary disease patients," *Eur. Respir. J.*, 2002, 20(3): 529-538.
Costa et al., "Influence of noninvasive ventilation by BiPAP® on exercise tolerance and respiratory muscle strength in chronic obstructive pulmonary disease patients (COPD)," *Rev. Lat. Am. Enfermagem.*, 2006: 14(3), pp. 378-382.
Díaz et al., "Breathing Pattern and Gas Exchange at Peak Exercise in COPD Patients With and Without Tidal Flow Limitation at Rest," *European Respiratory Journal*, 2001: 17, pp. 1120-1127.
Enright, "The six-minute walk test," *Resp. Care*, 2003: 8, pp. 783-785.
Ferreira et al., "Trigger Performance of Mid-level ICU Mechanical Ventilators During Assisted Ventilation: A Bench Study," *Intensive Care Medicine*, 2008,34:1669-1675.
Fink, "Helium-Oxygen: An Old Therapy Creates New Interest," *J. Resp. Care. Pract. now RT for Decision Makers in Respiratory Care*, 1999, pp. 71-76.
Gaughan et al., "A Comparison in a Lung Model of Low- and High-Flow Regulators for Transtracheal Jet Ventilation," *Anesthesiology*, 1992: 77(1), pp. 189-199.
Gregoretti, et al., "Transtracheal Open Ventilation in Acute Respiratory Failure Secondary to Severe Chronic Obstructive Pulmonary Disease Exacerbation," *Am. J. Resp. Crit. Care. Med.*, 2006: 173(8), pp. 877-881.
Haenel et al., "Efficacy of Selective Intrabronchial Air Insufflation in Acute Lobar Colapse," *Am. J. Surg.*, 1992: 164(5), pp. 501-505.
Keilty et al., "Effect of inspiratory pressure support on exercise tolerance and breathlessness in patients with severe stable chronic obstructive pulmonary disease," *Thorax*, 1994, 49(10): 990-994.
Köhnlein et al., "Noninvasive ventilation in pulmonary rehabilitation of COPD patients," Respir. Med., 2009, 103: 1329-1336.
Koska et al., "Evaluation of a Fiberoptic System for Airway Pressure Monitoring," *J. Clin. Monit.*, 1993: 10(4), pp. 247-250.
Lewis, "Breathless no. More, Defeating Adult Sleep Apnea," *FDA Consumer Magazine*, Jun. 1992, pp. 33-37.
Limberg et al., "Changes in Supplemental Oxygen Prescription in Pulmonary Rehabilitation," *Resp. Care*, 2006:51(11), p. 1302.
MacInryre, "Long-Term Oxygen Therapy: Conference Summary," *Resp. Care*, 2000: 45(2), pp. 237-245.
MacIntyre et al., "Acute exacerbations and repiratory failure in chronic obstructive pulmonary disease," *Proc. Am. Thorac. Soc.*, 2008: 5(4), pp. 530-535.
Massie et al., "Clinical Outcomes Related to Interface Type in Patients With Obstructive Sleep Apnea/Hypopnea Syndrome Who Are Using Continuous Positive Airway Pressure," *Chest*, 2003: 123(4), pp. 1112-1118.
McCoy, "Oxygen Conservation Techniques and Devices," *Resp. Care*, 2000: 45(1), pp. 95-104.
McGinley, "A nasal cannula can be used to treat obstructive sleep apnea"; *Am. J. Resp. Crit. Care Med.*, 2007: 176(2), pp. 194-200.
Menadue et al., "Non-invasive ventilation during arm exercise and ground walking in patients with chronic hypercapnic respiratory failure," *Respirology*, 2009, 14(2): 251-259.
Menon et al., "Tracheal Perforation. A Complication Associated with Transtracheal Oxygen Therapy," *Chest*, 1993: 104(2), pp. 636-637.
Messinger et al., "Tracheal Pressure Triggering a Demand-Flow CPAP System Decreases Work of Breathing," *Anesthesiology*, 1994: 81(3A), p. A272.
Messinger et al., "Using Tracheal Pressure to Trigger the Ventilator and Control Airway Pressure During Continuous Positive Airway Pressure Decreases Work of Breathing," *Chest*, 1995: vol. 108(2), pp. 509-514.
Mettey, "Use of CPAP Nasal Cannula for Aids of the Newborns in Tropical Countries," *Medecine Tropicale*, 1985: 45(1), pp. 87-90.
Nahmias et al., "Treatment of the Obstructive Sleep Apnea Syndrome Using a Nasopharyngeal Tube", *Chest*, 1988:94(6), pp. 1142-1147.
Nava et al., "Non-invasive ventilation," *Minerva Anestesiol.*, 2009: 75(1-2), pp. 31-36.
Passy-Muir Inc., "Clinical Inservice Outline", Apr. 2004, 19 pages.
Peters et al., "Combined Physiological Effects of Bronchodilators and Hyperoxia on Exertional Dyspnea in Normoxic COPD," *Thorax*, 2006: 61, pp. 559-567.
Polkey et al., "Inspiratory pressure support reduces slowing of inspiratory muscle relations rate during exhaustive treadmill walking in sever COPD," *Am. J. Resp. Crit. Care Med.*, 1996: 154(4, 10), pp. 1146-1150.
Porta et al., "Mask proportional assist vs pressure support ventilation in patients in clinically stable condition with chronic venilatory failure," *Chest*, 2002: 122(2), pp. 479-488.
Prigent et al., "Comparative Effects of Two Ventilatory Modes on Speech in Tracheostomized Patients with Neuromuscular Disease," *Am. J. Resp. Crit. Care Med.*, 2003: 167(8), pp. 114-119.
Puente-Maestu et al., "Dyspnea, Ventilatory Pattern, and Changes in Dynamic Hyperinflation Related to the Intensity of Constant Work Rate Exercise in COPD," *Chest*, 2005: 128(2), pp. 651-656.
Ram et al., "Non-invasive positive pressure ventilation for treatment of respiratory failure due to exacerbations of chroic obstructive pulmonary disease," *Cochrane Database Syst Rev.*, 2004(3):1-72.

(56) References Cited

OTHER PUBLICATIONS

Rothe et al., "Near Fatal Complication of Transtracheal Oxygen Therapy with the Scoop(R) System," *Pneumologio*, 1996: 50(10), pp. 700-702. (English Abstract provided.).

Rothfleisch et al., "Facilitation of fiberoptic nasotracheal intubation in a morbidly obese patient by simultaneous use of nasal CPAP," *Chest*, 1994, 106(1): 287-288.

Sanders et al., "CPAP Via Nasal Mask: A Treatment for Occlusive Sleep Apnea," *Chest*, 1983: 83(1), pp. 144-145.

Sinderby et al., "Neural control of mechanical ventilation in respiratory failure," *Nat. Med.*, 1999: 5(12), pp. 1433-1436.

Somfay et al., "Dose-Response Effect of Oxygen on Hyperinflation and Exercise Endurance in Nonhypoxaemic COPD Patients," *Eur. Resp. J.*, 2001: 18, pp. 77-84.

Sullivan et al., "Reversal of Obstructive Sleep Apnoea by Continuous Positive Airway Pressure Applied Through the Nares," *The Lancet*, 1981: 1(8225), pp. 862-865.

Sullivan, "Home treatment of obstructive sleep apnoea with continuous positive airway pressure applied through a nose-mask," *Bull Eur Physiopathol Respir.*, 1984: 20(1), pp. 49-54.

Tiep et al., "Pulsed nasal and transtracheal oxygen delivery," *Chest*, 1990: 97, pp. 364-368.

Tsuboi et al., "Ventilatory Support During Exercise in Patients With Pulmonary Tuberculosis Sequelae," *Chest*, 1997: 112(4), pp. 1000-1007.

*VHA/DOD Clinical Practice Guideline*, "Management of Chronic Obstructive Pulmonary Disease," Aug. 1999, Ver. 1.1a, Updated Nov. 1999.

Wijkstra et al., "Nocturnal non-invasive positive pressure ventilation for stable chronic obstructive pulmonary disease," *Cochrane Database Syst. Rev.*, 2002, 3: 1-22.

Yaeger et al., "Oxygen Therapy Using Pulse and Continuous Flow With a Transtracheal Catheter and a Nasal Cannula," *Chest*, 1994: 106, pp. 854-860.

Walsh, "McGraw Hill Pocket reference Machinists' and Metalworker' Pocket Reference," *New York McGraw-Hill*, 2000, pp. 3-67, submitting 3 pages.

International Preliminary Report and Written Opinion on Patentability for PCT/DE2004/001646, dated Jul. 3, 2006.

European patent Office Search Report issued Oct. 19, 2007 in co-pending EP 04762494.

International Search Report and Written Opinion for PCT/US04/26800 issued Jun. 22, 2006.

International Search Report and Written Opinion for PCT/US07/12108, dated Aug. 8, 2008.

International Search Report and Written Opinion for PCT/US07/17400, dated Apr. 28, 2008.

International Search Report and Written Opinion for PCT/US08/64015, dated Sep. 26, 2008.

International Search Report and Written Opinion for PCT/US08/64164, dated Sep. 29, 2008.

International Search Report and Written Opinion for PCT/US08/78031, dated Nov. 24, 2008.

International Search Report and Written Opinion for PCT/US08/78033, dated Dec. 3, 2008.

International Search Report and Written Opinion for PCT/US09/054673, dated Oct. 8, 2009.

International Search Report and Written Opinion for PCT/US09/41027, dated Dec. 14, 2009.

International Search Report and Written Opinion for PCT/US09/59272, dated Dec. 2, 2009.

International Search Report and Written Opinion for PCT/US2006/036600, dated Apr. 3, 2007.

International Search Report and Written Opinion for PCT/US2009/031355 issued Mar. 11, 2009.

International Search Report and Written Opinion for PCT/US2009/041034, dated Jun. 10, 2009.

International Search Report and Written Opinion for PCT/US2010/029871, dated Jul. 12, 2010.

International Search Report and Written Opinion for PCT/US2010/029873, dated Jun. 28, 2010.

International Search Report and Written Opinion for PCT/US2010/029874, dated Jul. 12, 2010.

International Search Report and Written Opinion for PCT/US2010/029875, dated Jul. 12, 2010.

International Search Report and Written Opinion for PCT/US2010/047920, dated Nov. 1, 2010.

International Search Report and Written Opinion for PCT/US2010/047921, dated Jan. 27, 2011.

International Search Report for PCT/DE2004/001646, dated Jan. 17, 2005.

International Search Report and Written Opinion for PCT/US2011/047994, dated Dec. 13, 2011.

International Search Report and Written Opinion for PCT/US2011/054446, dated Jan. 5, 2012.

\* cited by examiner

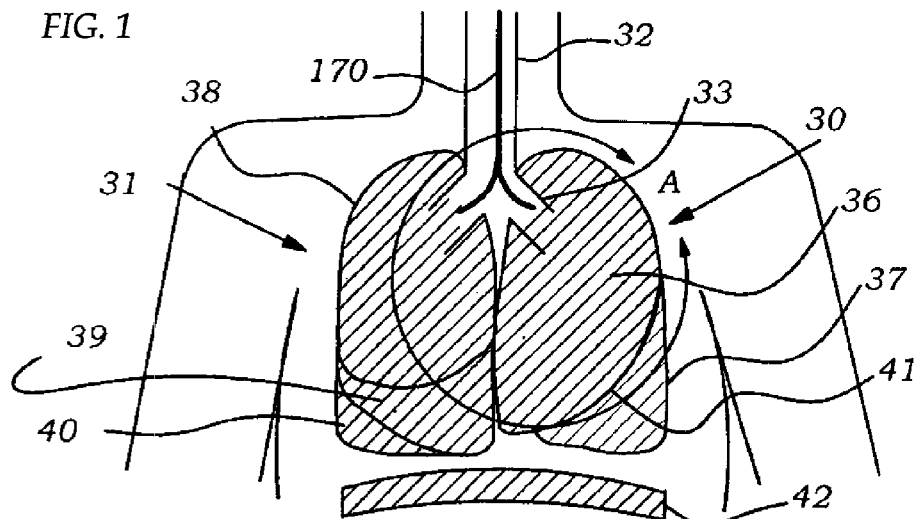
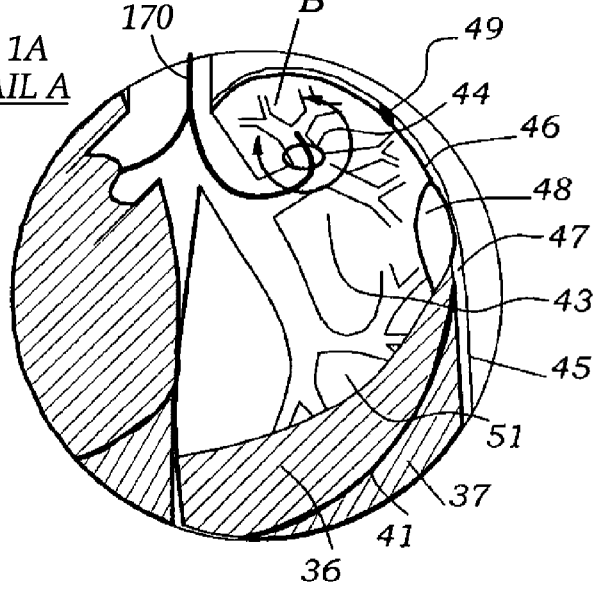
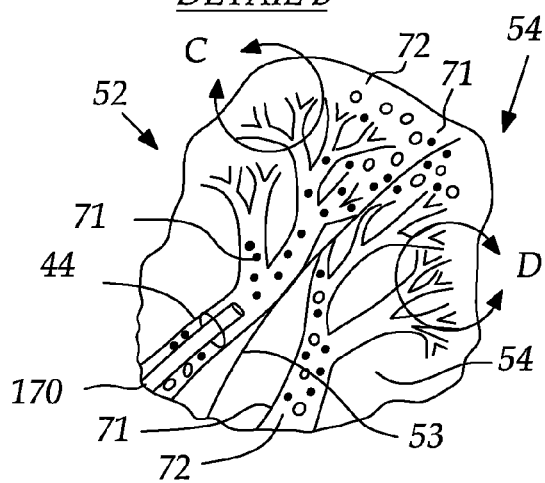
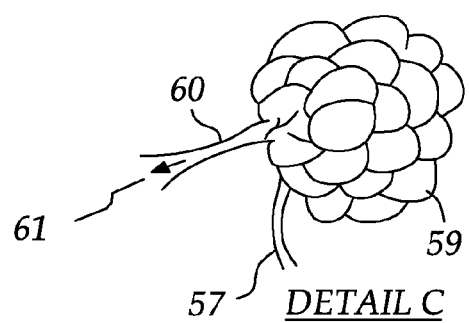
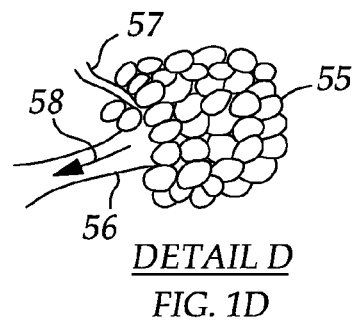
FIG. 1
FIG. 1A DETAIL A
FIG. 1B DETAIL B
DETAIL C FIG. 1C
DETAIL D FIG. 1D

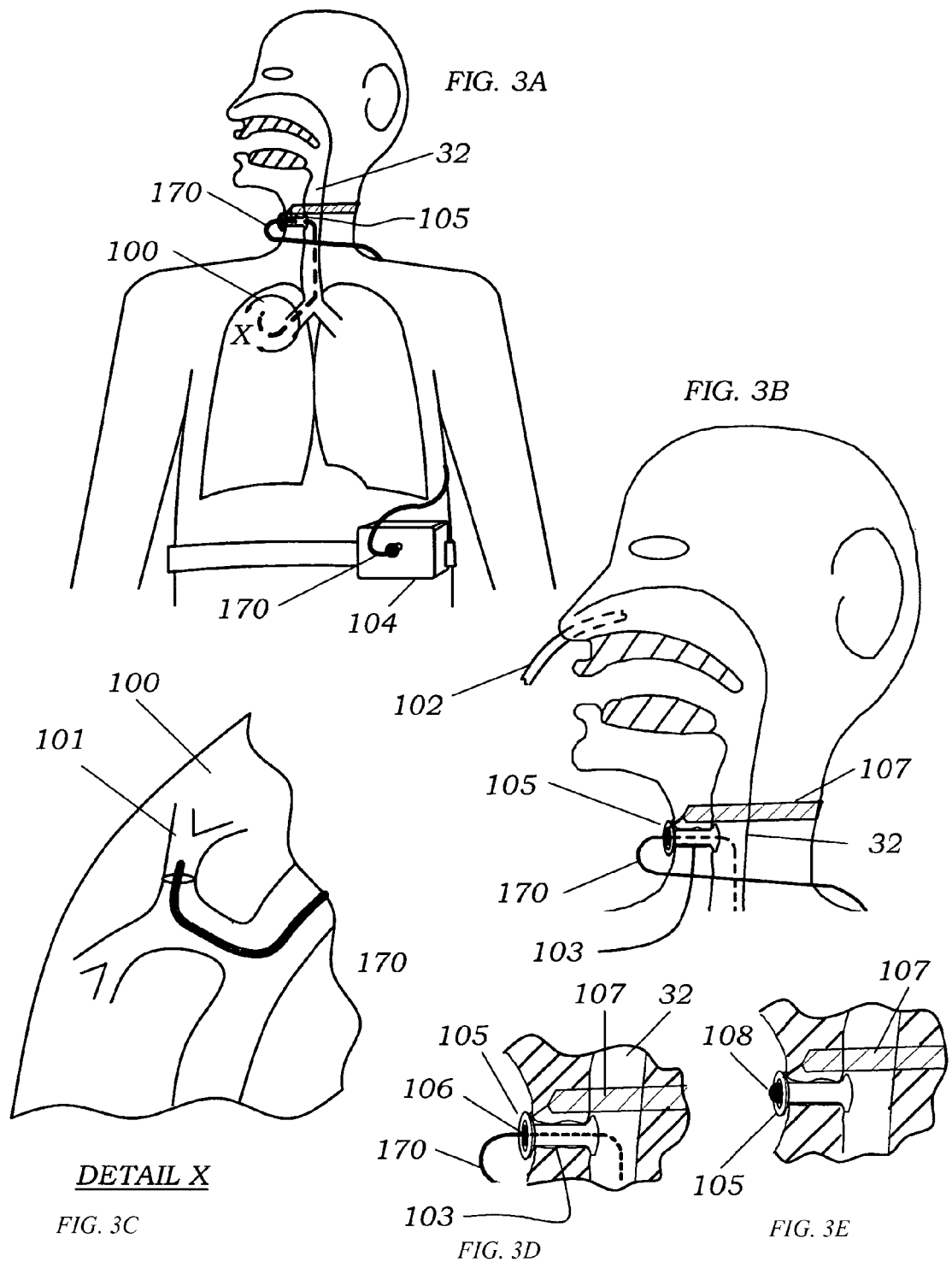

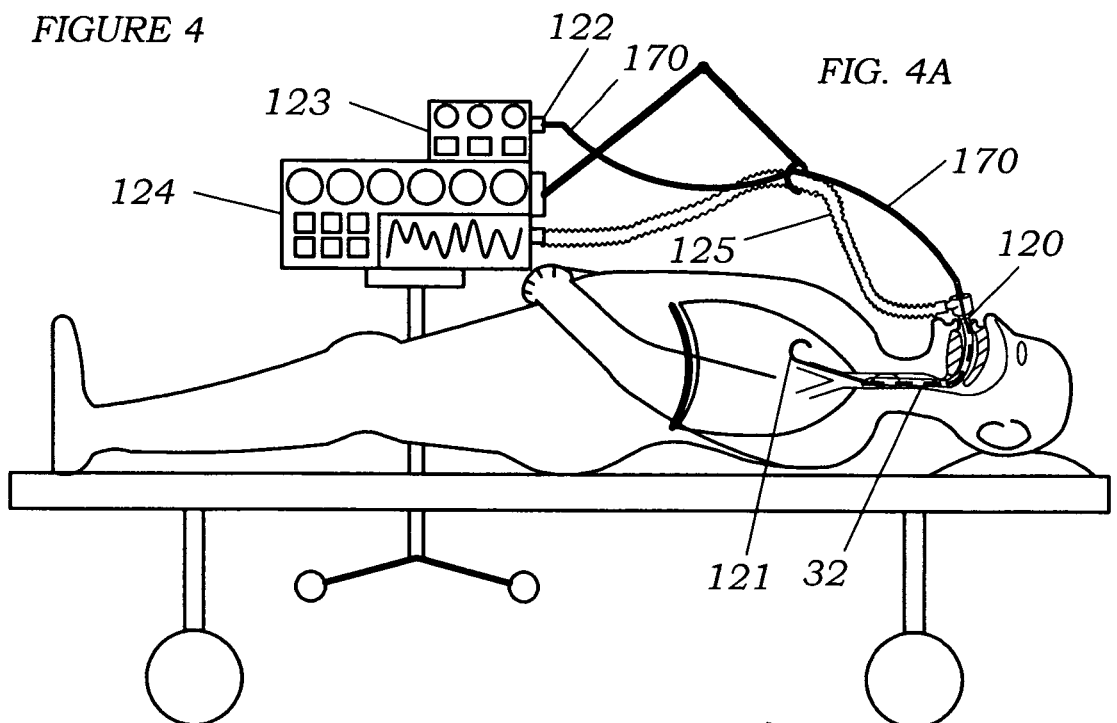
FIGURE 4
FIG. 4A
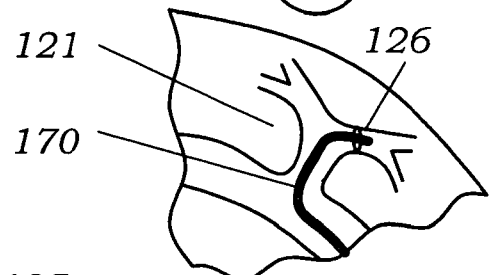
DETAIL W
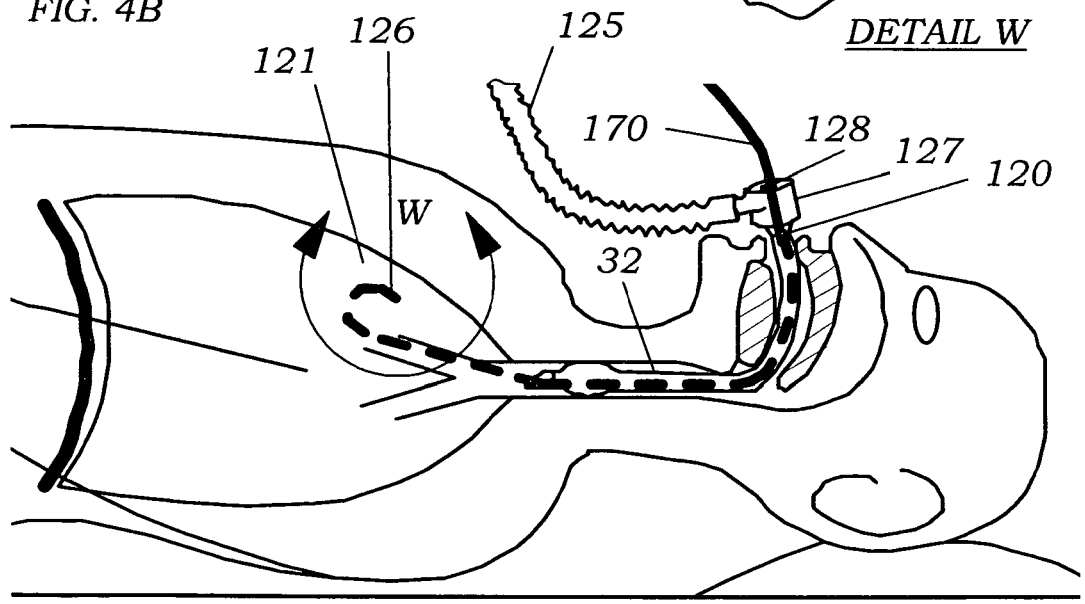
FIG. 4B

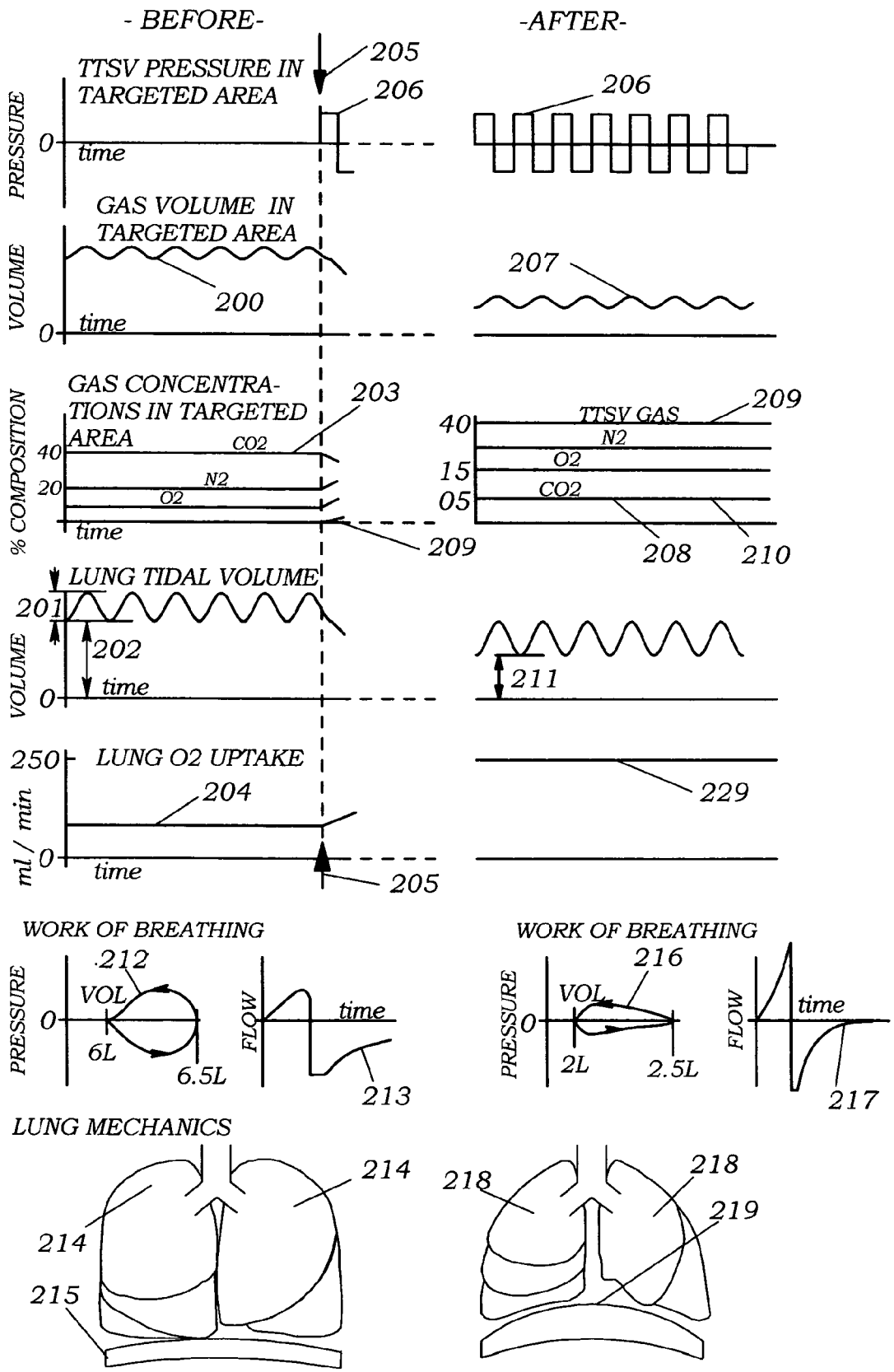

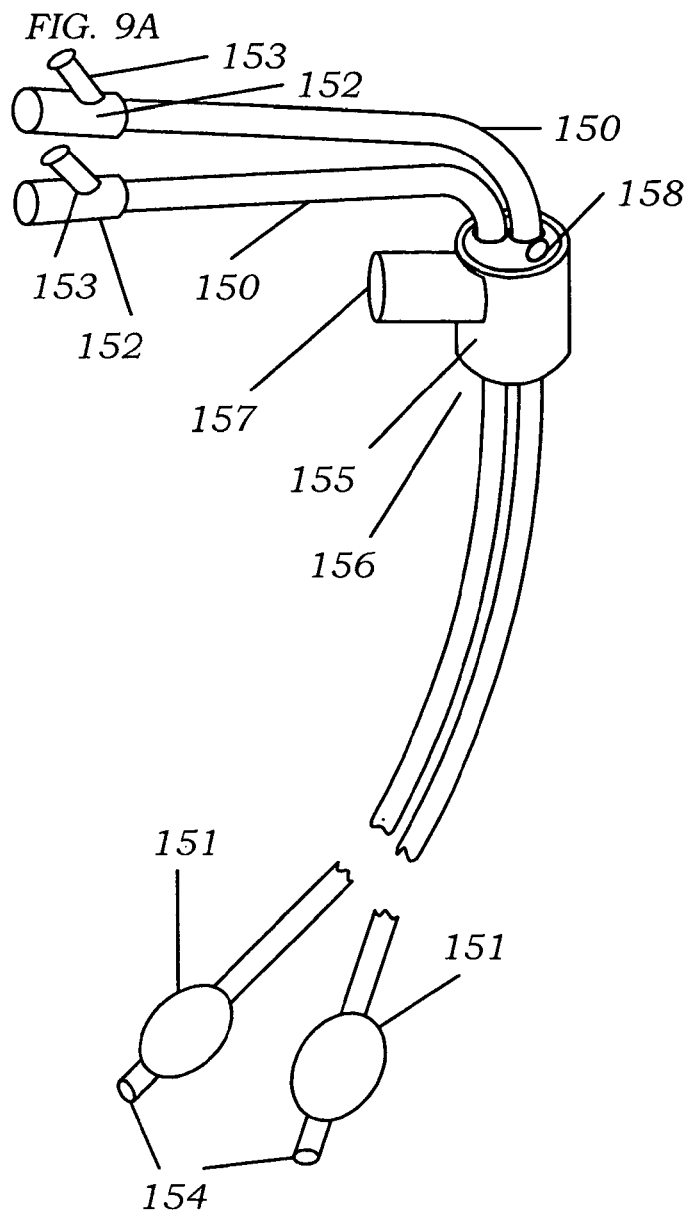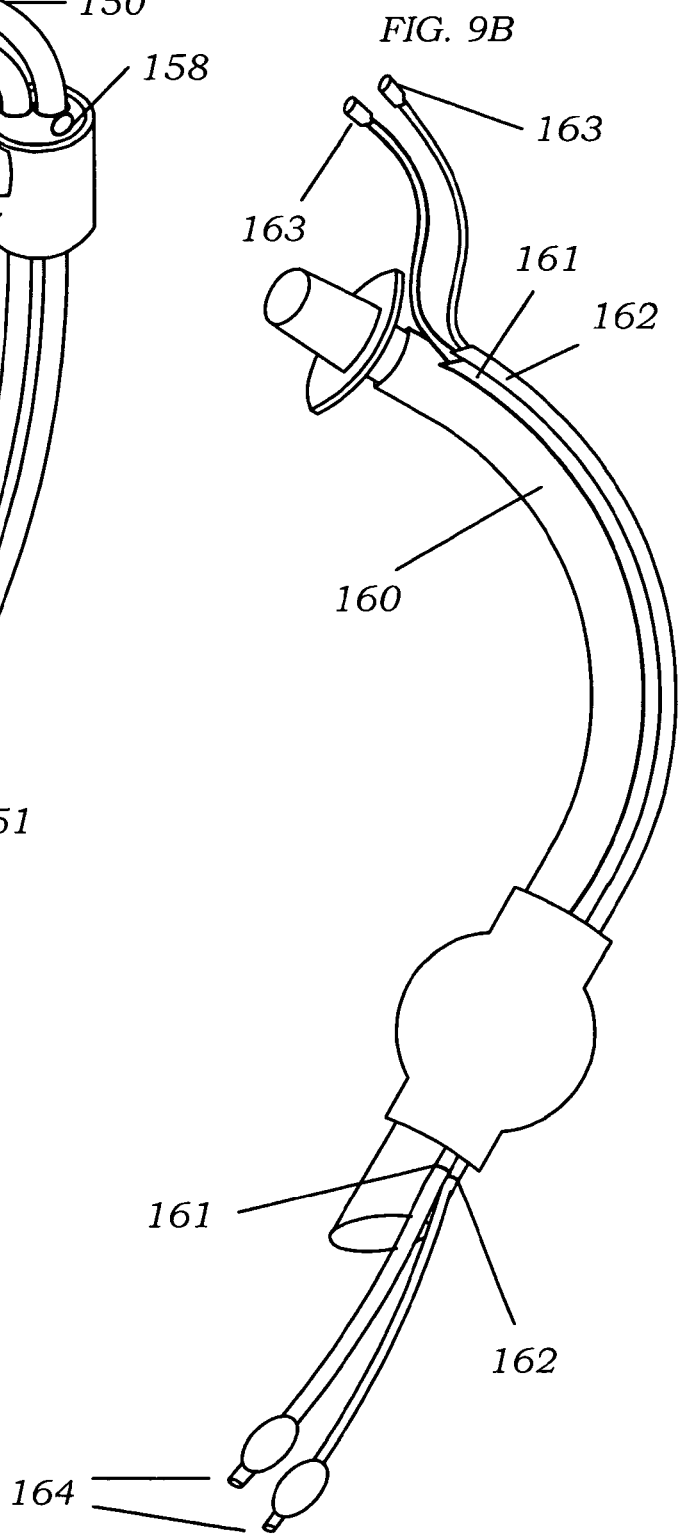

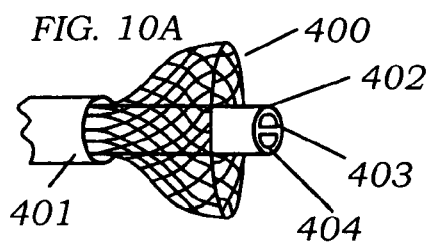
FIG. 10A
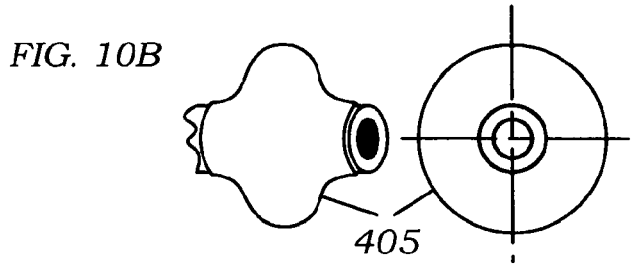
FIG. 10B
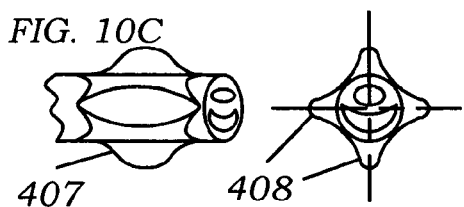
FIG. 10C
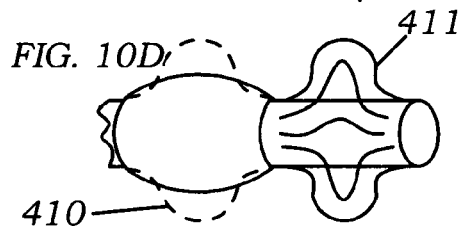
FIG. 10D
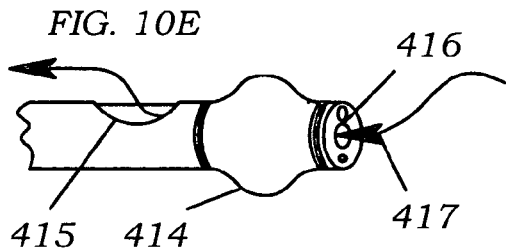
FIG. 10E
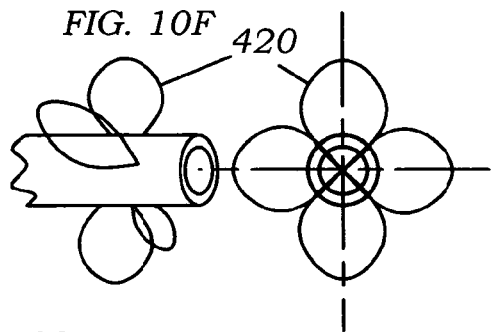
FIG. 10F
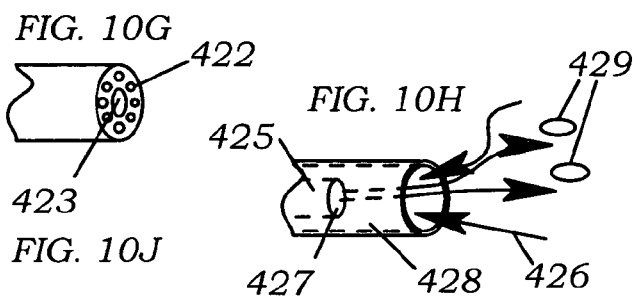
FIG. 10G  FIG. 10H
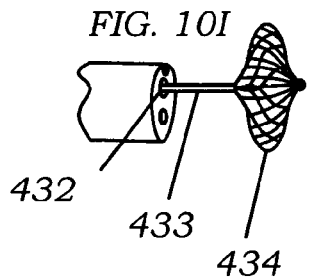
FIG. 10I
FIG. 10J
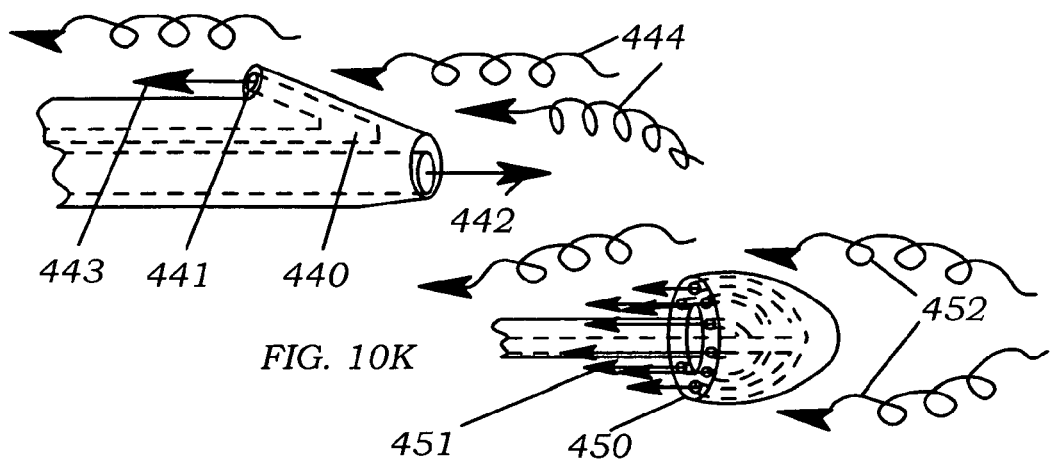
FIG. 10K

METHODS, SYSTEMS AND DEVICES FOR IMPROVING VENTILATION IN A LUNG AREA

CROSS-REFERENCE TO RELATED APPLICATIONS

This application is a Continuation of U.S. patent application Ser. No. 12/493,677, filed Jun. 29, 2009, which is a Continuation of U.S. patent application Ser. No. 10/870,849, filed Jun. 17, 2004, which claims priority to Provisional Patent Application No. 60/479,213, filed Jun. 18, 2003, all of which are incorporated herein in their entirety.

BACKGROUND OF THE INVENTION

The present invention relates to the field of respiratory therapy and specifically to the field of lung ventilation to treat a variety of pulmonary diseases.

Lung diseases are the number one category of diseases and a leading cause of death worldwide. Some lung diseases, such as Chronic Obstructive Pulmonary Disease (COPD), Acute Respiratory Distress Syndrome (ARDS), Severe Acute Respiratory Syndrome (SARS) and cystic fibrosis (CF) usually require some form of ventilation assistance or delivery of therapeutic agents in order to clinically improve the patient.

COPD in particular effects tens of millions of people and is one of the top five leading causes of death. COPD is a spectrum of problems, including bronchitis and emphysema, and involves airway obstruction, lung elasticity loss and trapping of stagnant $CO_2$-rich air in the lung. Emphysema, the worst form of COPD, occurs when there is a breakdown in the elasticity in the lung changing clusters of individual alveoli into large air pockets, thereby significantly reducing the surface area for gas transfer. In some cases air leaks out of the compromised walls of the minute airways to the periphery of the lung causing the membranous lining to separate and forming large air vesicles called bullae. Also due to elasticity loss, small conducting airways leading to the alveoli become flaccid and have a tendency to collapse during exhalation, trapping large volumes of air in the now enlarged air pockets, thus reducing bulk air flow exchange and causing $CO_2$ retention in the trapped air. Mechanically, because of the large amount of trapped air at the end of exhalation, known as elevated residual volume, the intercostal and diaphragmatic inspiratory muscles are forced into a pre-loaded condition, reducing their leverage at the onset of an inspiratory effort thus increasing work-of-breathing and dyspnea. Also, areas with more advanced emphysema and more trapped air tend to comprise the majority of the chest cavity volume and tend to fill preferentially during inspiration due to their low elasticity, thus causing the healthier portions to be disproportionately compressed rather than inflating normally during inspiration and receiving their share of inspired air. In emphysema therefore more effort is expended to inspire less air and the air that is inspired contributes less to gas exchange.

ARDS is a respiratory insufficiency caused by a variety of underlying problems such as lung injury, infection, edema, or atelectasis. SARS is a sudden respiratory insufficiency and appears to be caused by a viral infection. CF is a genetic condition in which airways secrete copious amounts of mucus and are inflamed.

Conventionally prescribed therapies for COPD and ARDS and sometimes SARS and CF include pharmacological agents (beta-agonists, aerosolized bronchodilators, anti-inflammatories and mucolytics), supplemental long term oxygen therapy (LTOT) delivered nasally or via tracheotomy, BiLevel Continuous Positive Airway Pressure (BiPAP), which lowers work of inspiration by providing a steady stream of pressure, Tracheal Oxygen Gas Insufflation (TGI), described by Christopher, *JAMA* 1986; 256: 494-7, which reduces $CO_2$ content in the upper airways thus allowing higher $O_2$ concentrations to reach the distal airways, respiratory muscle rehabilitation, pulmonary hygiene, such as lavage and percussion therapy, lung volume reduction surgery (LVRS) and lung transplantation (LX). These therapies all have certain disadvantages and limitations with regard to effectiveness, targeting accuracy, risk or availability. Usually, after progressive decline in lung function despite attempts at therapy, patients become physically incapacitated or sometimes require more invasive mechanical ventilation to survive in which case weaning from ventilator dependency is often times difficult. Conventional invasive ventilation modes include Continuous Mechanical Ventilation (CMV), Synchronized Intermittent Mechanical Ventilation (SIMV), Positive End Expiratory Pressure (PEEP) therapy, and high frequency jet ventilation (HFJV).

Some newer ventilatory methods have been studied in the attempt to improve treatment of COPD and ARDS. One such method described by Fink, *J. Resp Care Pract Apr* 1999; 71 is ventilation of a lung with gases of low molecular weights and low viscosity, such as helium-oxygen mixtures or nitric oxide, in order to decrease gas flow resistance and lower surface tension in distal airways and alveolar surfaces, thus increasing oxygen transfer across the alveolar surface into the blood. Another new method includes liquid perfluorocarbon ventilation which can displace mucus in distal airways while still conducting oxygen thus improving gas flow. Another method never successfully commercialized is Negative End Expiratory Pressure (NEEP), which helps remove CO2-rich gas during the exhalation cycle. These invasive methods typically ventilate COPD and ARDS patients more effectively then conventional invasive ventilation modes and may improve weaning, but they are significantly limited in efficacy because they can not easily be provided as chronic treatments and are not target specific. Rather they are inherently designed to treat the whole lung from the upper airway and hence do not address the significant problem of hyperinflation and areas of trapped stagnant gas, nor the problem of maldistribution of inspiratory gas volume.

Some additional devices and techniques have been invented with the aim of improving efficacy. U.S. Pat. No. 6,575,944 describes a catheter that is used for medication delivery through an endotracheal tube. That invention is good for pharmacological therapy on a mechanically ventilated patient, however the invention does not address the significant ventilation needs of the diseased lungs such as trapped gas and hyperinflated lungs.

U.S. Pat. No. 6,520,183 describes a catheter used to block on lung and delivery anesthesia to the other lung. That invention and other like it can only be used for one lung ventilation, almost always for surgery. That invention can be used in the unintended use of shunting ventilation to one lung, if the other lung is too diseased, however this usage would have significant limitations in that lobar or segmental sections of lung could not be individually blocked; hence this therapy would not be selective at all.

U.S. Pat. Nos. 6,227,200; 5,791,337; 5,598,840; 5,513,628; 5,460,613; 5,134,996; and 4,850,350 all describe catheters used for intermittently accessing and suctioning the trachea and main stem bronchi during through a tracheal tube during mechanical ventilation. That invention does not address the severe ventilation problems of the diseased lung, such as trapped air, hyperinflation, and poor airflow and perfusion distribution.

U.S. Pat. No. 5,904,648 describes a catheter for blocking airflow to one lung in order to ventilate and deliver anesthesia to the other side while the blocked side is being operated on. Again, that invention does not address improving ventilation and gas exchange.

U.S. Pat. Nos. 5,255,675 and 5,186,167 describe a catheter placed in the trachea through which the trachea is insufflated with oxygen. In clinical practice that invention and others like it have been proven to reduce the amount of CO2 in the lung and thus improve ventilation, however because the therapy described in this invention can inherently only be applied to the upper airways, it does nothing to improve the significant hyperinflation, air trapping and airflow and perfusion maldistribution of diseased lungs, and thus the therapy is severely limited. Indeed this therapy has not been well received clinically because the amount of benefit does not justify the added attention required.

U.S. Pat. No. 5,193,533 describes an invention similar to U.S. Pat. No. 5,255,675 in which high frequency ventilation is administered to the trachea to improve oxygenation. That invention has been proven clinically useful during short term medical procedures because the lung can be effectively mechanically ventilated at lower pressures but it is not useful as a subacute or chronic therapy as it does not reduce the air trapping, hyperinflation, or airflow and blood perfusion maldistribution.

U.S. Pat. Nos. 4,967,743; 4,838,255 and 4,825,859 describe a catheter for suctioning and lavaging the airways. That invention is limited to managing the airway integrity and pulmonary hygiene and is not suited for directly improving the underlying causes of air trapping, hyperventilation, and air flow maldistribution in the lung.

U.S Patent Application 20020179090 describes an aspiration catheter for removing phlegm from a lung. This invention is only useful in airway management and is not suited for directly improving the underlying causes of air trapping, hyperventilation, and air flow maldistribution in the lung.

U.S Patent Application 20010035185 describes a nasalpharyngeal catheter for delivering breathing gases to the pharynx to supplement regular ventilation or breathing. That invention is incrementally more effective than LTOT in that the gases are delivered more effectively but unfortunately the technique can not directly improve the underlying causes of air trapping, hyperventilation, and air flow maldistribution in the lung It must be emphasized that an effective ventilation treatment should ideally target specific areas of the lung that are most diseased yet all the methods described in the prior art employ ventilation on the entire lung as a whole, rather than on targeted lung areas that are more diseased. Therefore, all known ventilation modes allow trapped CO2 to persist in the worst effected areas of the lung and allow these areas to remain hyperinflated with the CO2-rich air, thus taking up valuable space in the chest cavity and compressing other potentially contributory lung areas. Other inventions or conventional therapies are either to traumatic, too transient, not site-specific, too experimental or not effective. The present invention disclosed herein addresses these shortcomings as will become apparent in the later descriptions.

BRIEF SUMMARY OF THE INVENTION

The present invention disclosed herein takes into consideration the problems and challenges not solved by the aforementioned prior art methods. In summary, this invention accomplishes (1) effective and direct cannulation of the lung area requiring treatment for a targeted site-specific treatment, (2) provides the option of sub-chronic or chronic treatment without the vigilance of a clinician, either in the hospital setting or in the home-care setting, and can be titrated accordingly, (3) is atraumatic, (4) improves hyperinflation and stagnant gas trapping in the distal spaces, (5) improves the maldistribution of airflow and blood perfusion, and (5) is cost effective.

The present invention provides a method for directly ventilating an area in a lung to improve the gas exchange in that area, typically for the treatment of COPD, although other respiratory diseases, such as ARDS, SARS, CF and TB may also benefit from this approach. The method, Trans-Tracheobronchial Segmental Ventilation (TTSV), is performed by (a) catheterizing the lung area with an indwelling catheter that can be left in place for extended periods without the vigilance of a clinician, and (b) ventilating the lung area via the catheter by delivering a ventilation gas and/or therapeutic substance such as a gas, liquid, solid or plasma, during an insufflation phase and removing waste and mixed gases from the area during an exhaust phase. The scientific principles employed to accomplish TTSV are fluid dynamics, the physical laws of mass transfer, i.e., gas and tissue diffusivity, gas concentration gradients and pressure gradients, as well as the physical laws of collapsible tubes and hemoglobin biochemistry laws.

In a preferred embodiment of the present invention the feeding bronchus of the targeted lung area is catheterized with an indwelling catheter anchored in the bronchus such that it can remain in place for extended periods without being attended by a person. The catheter enters the bronchial tree from the upper airway, either through an artificial airway such as a tracheal tube or through a natural airway such as the nasal passage or through a percutaneous incision such as a cricothyrotomy and is advanced to the targeted LUNG AREA through the bronchial tree with endoscopic or fluoroscopic guidance, where the tip is anchored in the airway. For ventilation and hygiene considerations, the catheter entry point into the body typically includes a self-sealing and tensioning connector that controls fluid from escaping from around the catheter shaft, but which permits the catheter to slide axially to compensate for patient movement or for elective catheter repositioning. The tensioning connector also serves to prevent inadvertent dislodging of the catheter's distal end anchor from the bronchus. In accordance with this embodiment the catheter includes at least one lumen through which the ventilation or therapeutic gas is delivered or insufflated directly into the targeted lung area and through which CO2-rich mixed gas is removed or exhausted from the targeted area. Gas removal from the area is typically enhanced by applying vacuum, as opposed to passive exhaust, however a low vacuum level is applied to avoid the collapse of airways and trapping gas behind the then collapsed airways. Optionally the segmental ventilation gas delivery/removal cycle is synchronized with the breathing pattern of the complete lung either during natural breathing or during mechanical ventilation but can also be asynchronous. The primary segmental ventilation parameters, flow, pressure and frequency, are regulated so as to create the desired volume delivery to the targeted area, or alternatively the desired pressure delivery to and in the targeted area, or still alternatively the desired gas composition in the targeted area or perfusion network thereof. The segmental ventilation parameters are measured to facilitate such regulation and to maintain safe conditions such as to prevent barotrauma.

Still in accordance with the preferred embodiment of the present invention, the fluid delivered to the targeted area may include standard breathing gases such as filtered air-oxygen mixtures, or may include therapeutic gases, such as helium, helium-oxygen mixtures, nitric oxide, other low molecular weight gases and gases enriched with particalized medicants, or may include liquids such as perfluorocarbons. Hereafter, the various fluids potentially used in TTSV will be referred to as simply 'ventilation gas'.

Still in accordance with the preferred embodiment of the present invention, the proximal end of the catheter is kept external to the patient and is connected to a segmental ventilation gas control unit. The gas control unit comprises a supply of ventilation gas, or alternately an input connection means to a supply thereof, and comprises the requisite valves, pumps, regulators, conduits, sensors and control electronics to control the desired pressure and/or flow delivery of the gas and to control the desired pressure in the lung area. The gas control unit may comprise a replaceable or refillable modular cartridge of compressed or concentrated ventilation gas and/or may comprise a pump system that receives ventilation gas from a reservoir and ejects the ventilation gas into the catheter at the desired parameters. The gas control unit further comprises fail-safe over-pressure relief mechanisms to protect against inadvertent lung barotrauma. The gas control unit also typically comprises a negative pressure generating source and control system also connectable to a lumen in the catheter for the previously described gas removal phase, i.e., exhaust phase, of the gas control unit ventilation cycle. The gas control unit may be configured to be remove-ably or permanently attached internally or externally to a standard lung ventilator, in the case of performing gas control unit on a mechanically ventilated patient, or may be an independent unit optionally to be worn by an ambulatory patient, in the case of performing TTSV on for example a home-based naturally breathing patient. It is appreciated that the gas control unit will have the requisite control and monitoring interface to allow the user to control and monitor the relevant parameters of the TTSV, as well as the requisite power source, enclosure, electronics, etc.

In an optional embodiment of the present invention, an average pressure is created in the targeted lung area which is slightly elevated compared to the average pressure in the remainder of the lung. This is achieved by measuring and regulating the lung area and TTSV parameters accordingly. The purpose of the elevated pressure is four fold: (1) it will facilitate a dilitation of the distal airways to facilitate communication of the ventilation gas with the otherwise poorly communicating lung lobules and alveoli; (2) it will facilitate $CO_2$ displacement out of the elevated pressure area into areas of lower pressure due to simple flow and pressure gradient laws; (3) it will facilitate displacement of $CO_2$-rich gas out of very distal areas through collateral channels at the alveolar and lobular level into neighboring lung areas; (4) it will increase the rate of ventilation gas diffusion across the alveolar surface into the blood due to higher gas partial pressures, obeying diffusivity laws and hemoglobin biochemistry laws. Conversely, the average pressure created in the targeted area can also be regulated to produce a slightly lower average pressure than the remainder of the lung, in order to facilitate volume reduction of the targeted hyperinflated area.

TTSV can be performed by delivering ventilation gas to the targeted area but without applying an active exhaust phase as opposed to the previously described active exhaust phase. Or, alternatively, active insufflation and expiratory phases can simultaneously co-exist, rather than alternating between phases. Still alternately gas delivery and active gas exhaust can be continuous or semi-continuous rather than alternating with discrete phases of off and on. In any case, insufflation gas pressure and flow can be delivered continuously, variably, intermittently at low frequency, <20 cycles/min., intermittently at medium frequency, 20-50 cycles/min., intermittently at high frequency, >50 cycles/min., or synchronized with the patient's breathing cycle in order optimize the airflow fluid dynamics of TTSV. In the case of non-active expiration, the $CO_2$-rich gas is simply displaced by the insufflation gas and exits the targeted lung area passively due to concentration and pressure gradients. It can be appreciated that the possible combinations of pressure amplitudes and frequency profiles of both delivered and exhausted gases are extensive, but all must comply with the following fundamental and critical principle that is unique to the present invention: The regulated parameters must produce a decrease in stagnant gas in the treated area, produce an increase in beneficial gas in the treated area, avoid excessive or unsafe pressure and volume increases in the treated area, and ideally reduce the volume in the treated area to redistribute inspired air to other healthier lung areas.

In a second general embodiment of the present invention, regulation of the pressure in the ventilated segment is further facilitated by occluding the annular space between the catheter and the feeding bronchus of the ventilated segment. This embodiment further facilitates control of the pressure and gas concentration in the targeted lung area particularly in gravitationally challenging situations, for example when a non-gaseous substance is used in the ventilation fluid, or when a low molecular weight gas is used.

In a third general embodiment of the present invention, TTSV of targeted lung area is performed using gas removal only, rather than both gas delivery and gas removal. In this embodiment can be accomplished by applying, via the catheter, a vacuum to the area, or can be accomplished by creating a venturi effect by establishing a high velocity gas jet of positive pressure in the proximal direction to entrain gas out of the targeted lung area. The vacuum created by these later embodiments is typically very low level to avoid bronchial collapse, which may be determined by measuring gas flow and adjusting the vacuum level accordingly. Again, this form may be continuous, intermittent or variable and can be synchronized with the breathing cycle. It is understood that either form of gas evacuation will include the appropriate modifications to the gas control unit previously described.

In forth general embodiment of the present invention, a ventilation gas is delivered via the catheter into the targeted area for a desired period after which a vacuum is applied via the catheter to the bronchii feeding the targeted area also for a desired period. The vacuum amplitude is selected to collapse the bronchii thus trapping the ventilation gas in the area. Mixed gases are forced out during the ventilation gas delivery phase and also a portion of mixed gases are sucked out of the conducting airways immediately before their collapse at the beginning of the vacuum phase. The sequence is repeated successively until a predominant concentration of ventilation gas and minority of native gas occupies the area.

In a fifth general embodiment of the present invention, in order to improve ventilation in the lung as a whole, a segment which is not contributing much to gas exchange is blocked with an occlusive catheter to shunt inspired gas to other areas of the lung that are less diseased. Known as Trans-Tracheobronchial Segmental Shunting (TTSS), this embodiment can be useful considering that the more diseased less elastic areas preferentially fill with inspired air which does not reach the alveoli because of the large amount of stagnant trapped gas. TTSS can be performed continuously, semi-continuously, dynamically, or intermittently, or synchronized with the patients breathing cycle. TTSS can also be performed concurrently with some level of active gas removal using vacuum, and therapeutic gas or agent delivery into the blocked targeted area through the TTSS catheter. TTSS can also be performed with intermittent removal of the shunt but without removal of the catheter.

It should be noted that in some applications and embodiments of this invention, the TTSV or TTSS procedure is performed as a temporary palliative procedure with dramatic clinical benefit during the actual therapy but with a dissipating benefit after the therapy is discontinued. In other applications and embodiments, TTSV or TTSS is performed during mechanical ventilation to more effectively ventilate a patient, for example acutely to wean a patient from ventilatory support, or subchronically or chronically to improve ventilation in ventilatory-dependent patients. Still in other cases, TTSV or TTSS is performed on a naturally breathing patient as a chronic therapy either continuously or intermittently in order to provide clinical benefit lasting periods of weeks or even years. In this later embodiment, the catheter may be removed after a treatment while leaving a hygienic seal at the percutaneous access point, and a new catheter later inserted for a subsequent treatment. A guidewire might be left in place to ease subsequent re-catheterization. It should also be noted that the TTSV or TTSS procedure may be performed simultaneously on different lung areas or sequentially on the same or different lung areas. It should also be noted that TTSV or TTSS can be extremely useful for gradually reducing bulla in bullous emphysema, particularly if a stream of low molecular weight gas such as HeliOx is insufflated into the targeted lung area and mixed gases are removed with aspiration. Finally it should be noted that the TTSV or TTSS procedure can be performed on a relatively few large sections of lung, for example a lobe or a few lobar segments on patients with heterogeneous or bullous emphysema, or can be performed on many relatively small sections of lung, for example twelve sub-subsegments on patients with diffuse homogeneous emphysema. The procedure and treatment can even be performed on an entire lung by catheterizing a left or right mainstem bronchus, or both lungs by catheterizing the trachea.

As previously noted no methods exist in the prior art wherein a poorly functioning lung area with trapped $CO_2$-rich gas is more effectively ventilated by directly delivering ventilation gases to that area and/or removal of CO2-rich gas from that area, or of bronchial shunting of inspired air from a local lung area to other lung regions.

It should be noted that while preferred and optional embodiments of the present invention are described, there are other useful embodiments not specifically stated but are implied as part of the present invention which combine various features of the described embodiment.

BRIEF DESCRIPTION OF THE DRAWINGS

FIG. 1 describes the anatomy of a lung and placement of the TTSV catheter.

FIG. 3 depicts TTSV therapy on a naturally breathing patient.

FIG. 4 depicts TTSV therapy during mechanically ventilation.

FIG. 5 describes the effect of TTSV therapy on a naturally breathing patient.

FIG. 9 describes typical TTSS catheters.

FIG. 10 describes optional TTSV and TTSS catheter configurations.

DETAILED DESCRIPTION OF THE INVENTION

Figure 2A:
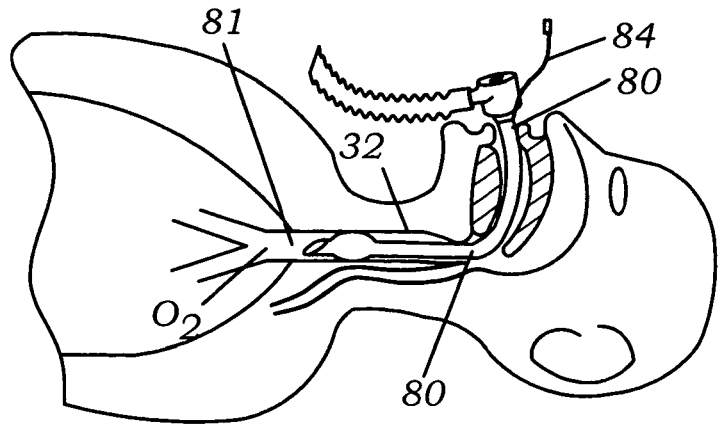
FIG. 2 describes conventional ventilation therapies for treating compromised lungs.

Referring to FIG. 1 the lung anatomy is described including the left 30 and right 31 lung, trachea 32, the left main stem bronchus 33, the five lung lobes 36, 37, 38, 39, 40, a lateral fissure 41 separating the left upper and lower lobe, and the diaphragm 42 which is displaced downward indicative of a hyperinflated emphysematous lung. FIG. 1a shows a cut away view of the left upper lobe bronchus 43, the apical segmental bronchus 44 of the left upper lobe, the parietal pleura 45, the visceral pleura 46 and the pleural cavity 47. Large bulla 48 are membranous air vesicles created on the surface of the lung between the visceral pleura 46 and lung parenchyma 51 due to leakage of air out of the damaged distal airways and through the lung parenchyma. The air in the bullae is highly stagnant and does not easily communicate with the conducting airways making it very difficult to collapse bullae. Pleural adhesions 49 are fibrous tissue between the visceral pleura 46 and the parietal pleura 45 which arise from trauma or tissue fragility. These adhesions render it difficult to acutely deflate an emphysematous hyperinflated lung compartment without causing tissue injury such as tearing, hemorrhage or pneumothorax. FIG. 1b shows an exploded view of the upper lobe apical segment 52 and the anterior segment 54. FIG. 1d describes a non-emphysematous lung lobule which includes the functional units of gas exchange, the alveoli 55, and CO2-rich exhaled gas 58 easily exiting the respiratory bronchiole 56, Also shown are intersegmental collateral channels 57, typically 40-200 um in diameter, which communicate between bronchopulmonary segments making it difficult for a lung compartment to collapse or remain collapsed because of re-supply of air from neighboring compartments through these collateral channels. Detail C in FIG. 1c describes an emphysematous lung lobule in which the alveolar walls are destroyed from elastin breakdown resulting in large air sacks 59. The emphysematous lobule traps air becoming further hyperinflated because the respiratory bronchiole leading to the engorged lobule collapses 60 during exhalation, thus allowing air in but limiting air flow out 61.

FIG. 1 also shows the TTSV catheter 170 anchored in the apical segment bronchus 44. In FIG. 1b, the TTSV ventilation gas 71 is shown being delivered by the TTSV catheter 170. The native gas 72 in the targeted apical segment is forced out of the apical segment 52 proximally alongside the catheter 170 and also across intersegmental collateral channels into the neighboring anterior segment 54 then proximally up the airways. The native gas may also be sucked proximally up the catheter. The TTSV parameters are regulated to produce the desired pressure, volumes and gas concentrations.

Figure 2B:
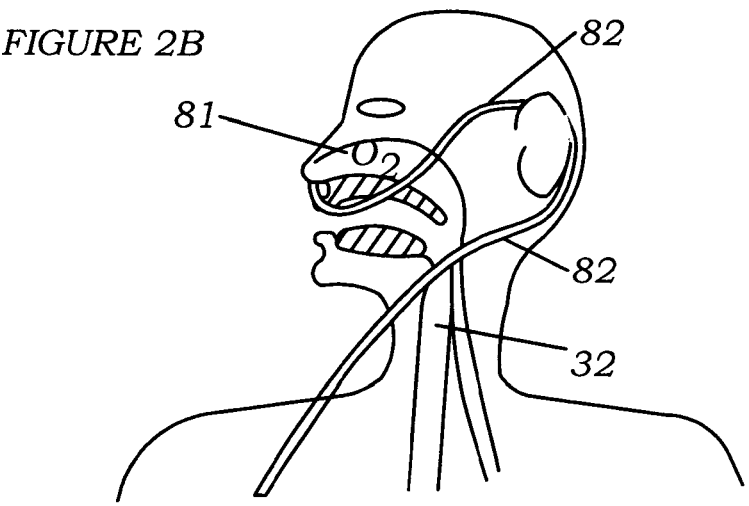
Figure 2C:
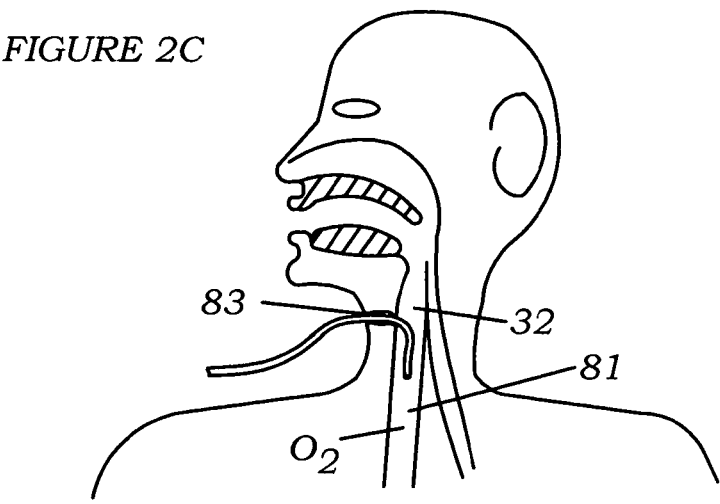

In FIG. 2 conventional therapies are shown which enhance gas exchange of a compromised lung. FIG. 2a shows mechanical ventilation in conjunction with Transtracheal Gas Insufflation (TGI) using an EndoTracheal Tube 80. Positive pressure is delivered to the lung via a mechanical ventilator and EndoTracheal Tube and the trachea 32 is insufflated with oxygen 81 via a dedicated lumen 84 in the EndoTracheal Tube to flush out retained CO2 in the trachea. This therapy does not address the stagnant gas in the hyperinflated lung areas that compromise ventilation. FIG. 2b shows long term oxygen therapy (LTOT) where oxygen 81 is delivered via nasal cannula 82. Again, while increasing O2 levels in the lung's upper airways, this therapy does not address the stagnant gas in the hyperinflated lung areas that compromise ventilation. FIG. 2c shows transtracheal oxygen therapy (TTOT) wherein oxygen 81 is delivered directly into the trachea 32 via a tracheotomy 83. While slightly more effective than LTOT, TTOT still has the same inherent shortcomings noted.

FIG. 3 describes a general layout of the invention disclosed herein, wherein TTSV or TTSS is performed on an ambulatory spontaneously breathing patient, showing percutaneous access into the trachea 32, catheterization of the targeted lung area 100, distal end anchoring 101, entry of the catheter 170 either nasally 102 or through a percutaneous incision 103, connection of the proximal end of the catheter to the wearable portable Gas Control Unit 104, in the case of TTSV therapy. Referring to FIG. 3b a cross-sectional view is shown of entry of the catheter into the patient showing a percutaneous connector 105 with a through-port and hygienic seal 106 and a securing means 107 fastening the seal to the neck of the patient. The hygienic seal 106 also prevents inadvertent unwanted axial movement of the catheter but allows desired axial sliding of the catheter in response to anticipated patient movement. The seal can be left in place to temporarily seal the incision with a self-sealing membrane or by attaching a plug 108 if the catheter is removed for extended periods.

FIG. 4 describes a general layout of the invention, wherein TTSV or TTSS is performed on a ventilatory dependent patient, showing entry of the catheter 170 through an endotracheal tube 120 which is in the trachea 32 of the patient, catheterization of the targeted lung area 121, connection of the proximal end of the catheter 122 to the ventilation Gas Control Unit 123, in the case of TTSV, as well as the ventilator 124 and breathing circuit 125. It can be seen that the catheter distal end is anchored 126 in the targeted bronchus and the catheter shaft at the patient entry point near the elbow connector 127 is tensioned 128 to prevent inadvertent unwanted movement with a tensioning and/or sealing means.

Figure 6:
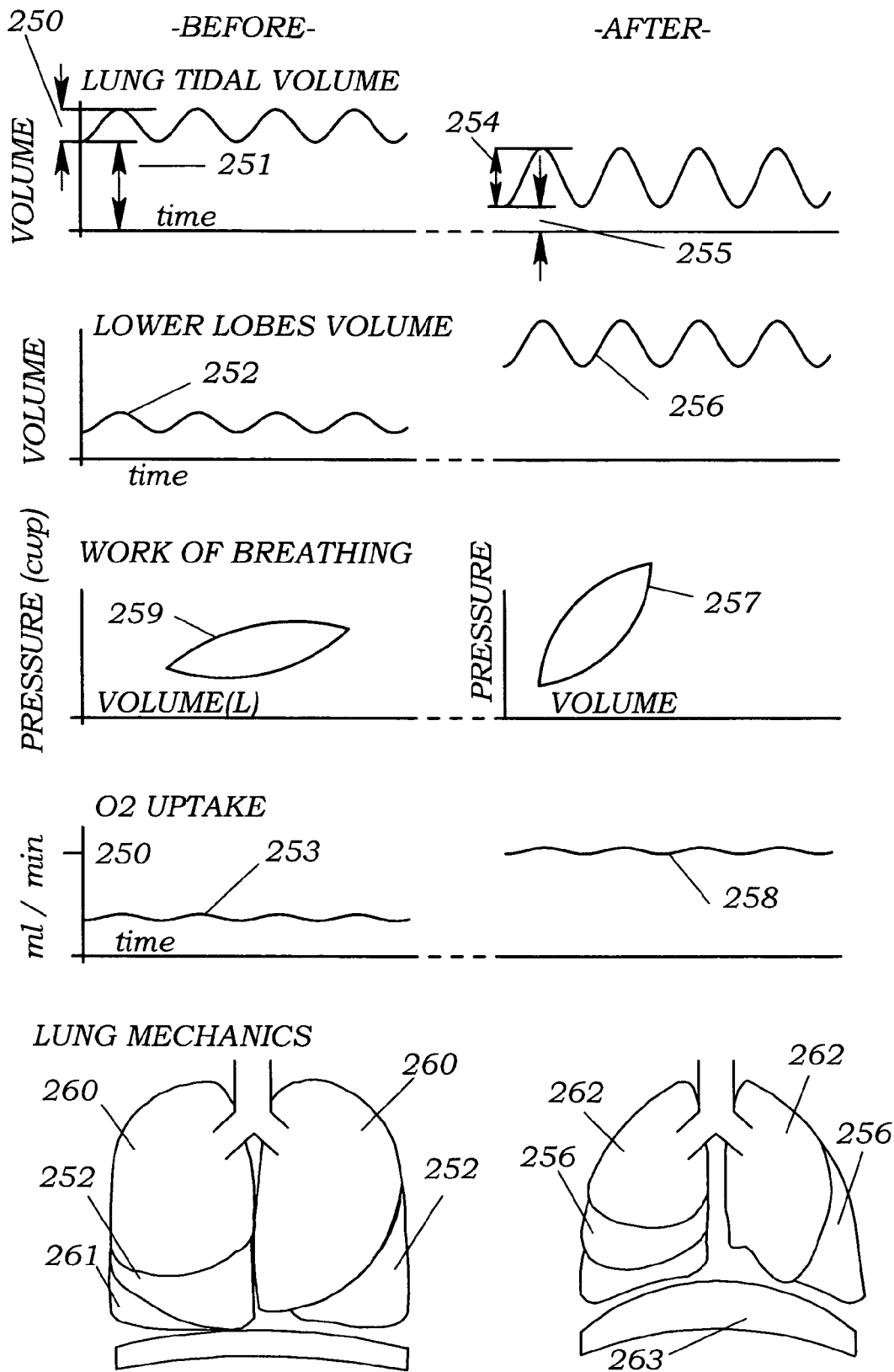
FIG. 6 describes the effect of TTSS therapy on a mechanically ventilated patient.
Figure 7A:
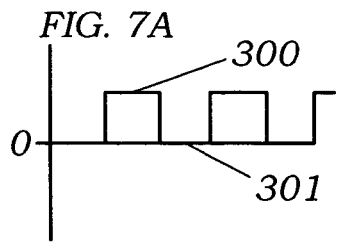
FIG. 7 describes optional TTSV treatment parameters.
Figure 7B:
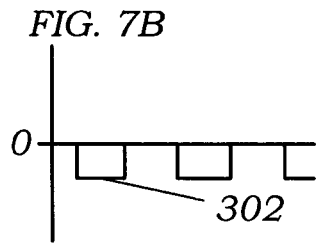
Figure 7C:
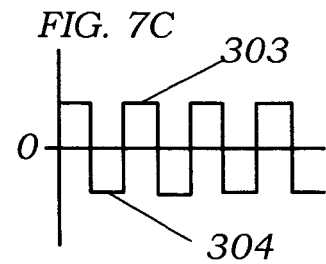
Figure 7D:
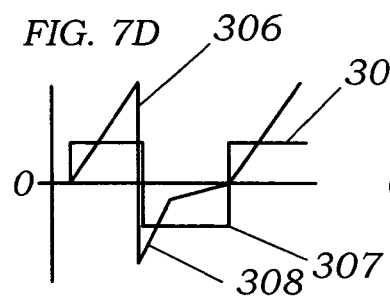
Figure 7E:
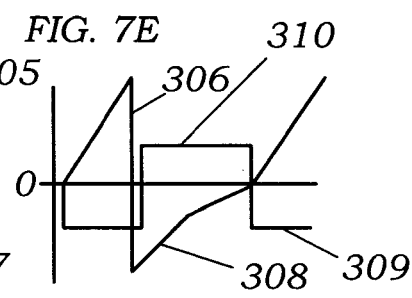
Figure 7F:
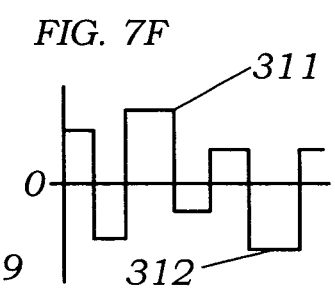
Figure 7G:
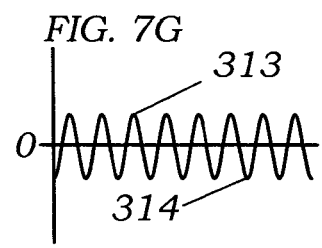
Figure 7H:
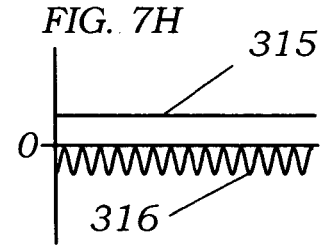
Figure 7I:
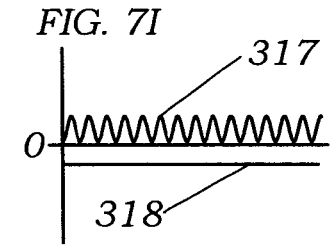
Figure 7J:
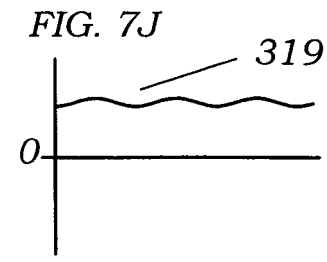
Figure 7K:
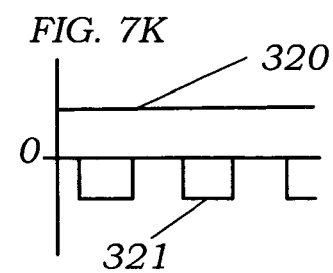
Figure 7L:
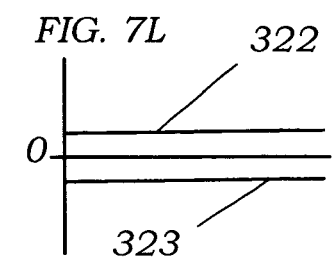
Figure 7M:
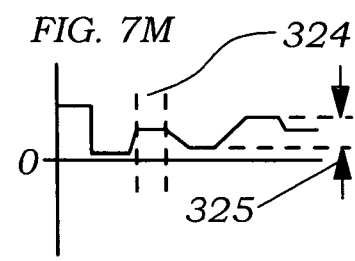
Figure 7N:
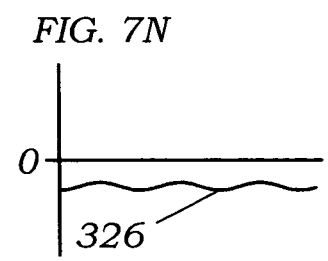
Figure 7O:
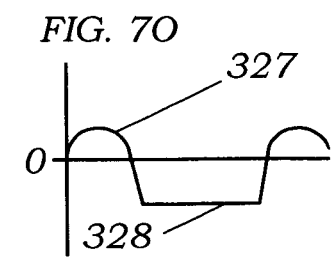

FIG. 5 graphically describes the effect of TTSV therapy performed on a naturally breathing patient. At baseline conditions the targeted lung area has an elevated gas volume 200 and the total lung has a tidal volume 201 with elevated residual volume 202. Due to gas trapping the targeted area has a predominant concentration of CO2-rich 203 stagnant gas with very little fresh CO2 coming from the blood stream, low blood perfusion due to shunting of blood to other lung areas, known as the Euhler reflex, and low O2 uptake 204. Work of breathing pressure-volume curves 212 of a breath indicate gas trapping and labored inspiration and exhalation. Breath air flow indicates a protracted exhalation 213 due to the poor lung elastic recoil. The lung itself has hyperinflated upper lobes 214 and diaphragm displaced downward 215. TTSV is commenced 205 by site-specific ventilation 206 of the targeted area, typically using 100% Oxygen or HeliOx or some other therapeutic gas delivered through the indwelling TTSV catheter. After therapeutic equilibrium, the targeted area gas volume is decreased 207, the native stagnant gas concentration in the targeted area is reduced dramatically 208 and is replaced by a high concentration of therapeutic gas 209 and fresh CO2 from the blood stream 210. Further, total lung residual volume decreases towards normal 211, O2 transfer increases 209 towards the normal value of 250 ml/min, work of breathing is less labored 216 and exhalation flow rate returns quickly to zero 217 due to improved recoil. The lung itself is less hyperinflated 218 and the diaphragm position returns toward normal 219. Depending on the parameters selected and other clinical factors, the therapeutic conditions can reach equilibrium in 30 minutes to 72 hours FIG. 6 graphically describes the effect of TTSS therapy performed on a mechanically ventilated patient. At baseline conditions the tidal volume in the lung 250 shows an elevated residual volume 251 and the volume in the lower lobes is abnormally low 252. Work of breathing shows poor or high lung compliance 259 in ml/cm H2O, and the overall gas exchange is comprised 253. The lung itself is hyperinflated, especially the upper lobes 260 and the diaphragm is displaced downward 261. After commencement of TTSS therapy the conditions begin to change due to the blocking of the targeted area by the blocking catheter, and optionally enhanced by applying a slight vacuum to the blocked area via the catheter. Due to absorption of the gas in the blocked area, or dissipation of the gas out of collateral channels, or by slight vacuum applied via the catheter, the volume in the targeted area decreases as does the overall lung volume 254 and lung residual volume 255. Some inspired gas volume is now diverted to the lower lobes 256, the lung compliance now decreases to a more healthy or elastic level 257 as shown by the pressure-volume curve of a breath, gas transfer returns to a more normal level 258, and the lung itself is less hyperinflated 262 and the diaphragm returns to a more normal position 263. Equilibrium can be reached between 30 minutes and 72 hours, depending on the targeted area blocked and other clinical conditions.

FIG. 7 graphically describes optional TTSV ventilation parameters with the abscissa and vertical coordinates corresponding to time and TTSV catheter pressure. FIG. 7a shows intermittent gas delivery with on 300 and off 301 times. FIG. 7b shows intermittent gas removal 302 by suctioning. FIG. 7c shows alternating gas delivery 303 and gas suctioning 304. FIG. 7d shows alternating gas delivery and suctioning synchronized with the breath cycle so that TTSV gas delivery 305 occurs during the inspiratory phase 306 and TTSV gas removal 307 occurs during the expiratory phase 308. FIG. 7e shows TTSV gas removal 309 synchronized with inspiration 306 and TTSV gas delivery 310 synchronized with exhalation 308. FIG. 7f shows changing levels and periods of TTSV gas delivery 311 and gas suctioning 312 wherein the levels are changing in order to maintain the desired conditions in the targeted area. FIG. 7g shows high frequency oscillatory gas delivery 313 and gas suctioning 314. FIG. 7h shows constant or static gas delivery 315 concurrent with high frequency oscillatory gas suctioning 316. FIG. 7i shows high frequency oscillatory gas delivery 317 concurrent with constant or static gas suctioning 318. FIG. 7j shows constant gas delivery 319 without any gas suctioning. FIG. 7k shows constant gas delivery 320 concurrent with intermittent gas suctioning 321. FIG. 7l shows concurrent constant gas delivery 322 and gas suctioning 323. FIG. 7m shows variable gas delivery periods 324 and amplitudes 325 in order to regulate the desired conditions in the targeted area. FIG. 7n shows constant or static vacuum 326 applied to the targeted lung area with out any gas delivery. FIG. 7o shows alternating gas delivery and gas suctioning with a short delivery phase 327 and extended vacuum phase 328.

Typical gas delivery and gas suction parameters depend on the area being treated and the clinical conditions. During mechanical ventilation, gas delivery can range from 0.1 to 1.5 lmp and 8 to 40 cmH2O at the lobar segment level and 1.0 to 10.0 lmp and 10 to 50 cmH2O at the tracheal level. Gas evacuation can range from 0.1 to 1.5 lmp and −5 to −40 cmH2O at the lobar segment level and 1.0 to 10.0 lmp and −10 to −50 cmH2O at the tracheal level. During spontaneous ventilation, flow can range from 0.05 to 1.5 lmp and 3 to 20 cmH2O at the lobar segment level and 1.0 to 10.0 lmp and 5 to 30 cmH2O at the tracheal level. Gas evacuation can range from 0.05 to 1.5 lmp and −3 to −20 cmH2O at the lobar segment level and 1.0 to 10.0 lmp and −5 to −30 cmH2O at the tracheal level. Frequencies can range from 1 to 120 cycles per hour if being used intermittently, and 2 to 120 cycles per minute in oscillatory mode, and 1 hour to indefinite durations for continuous mode.

Figure 8:
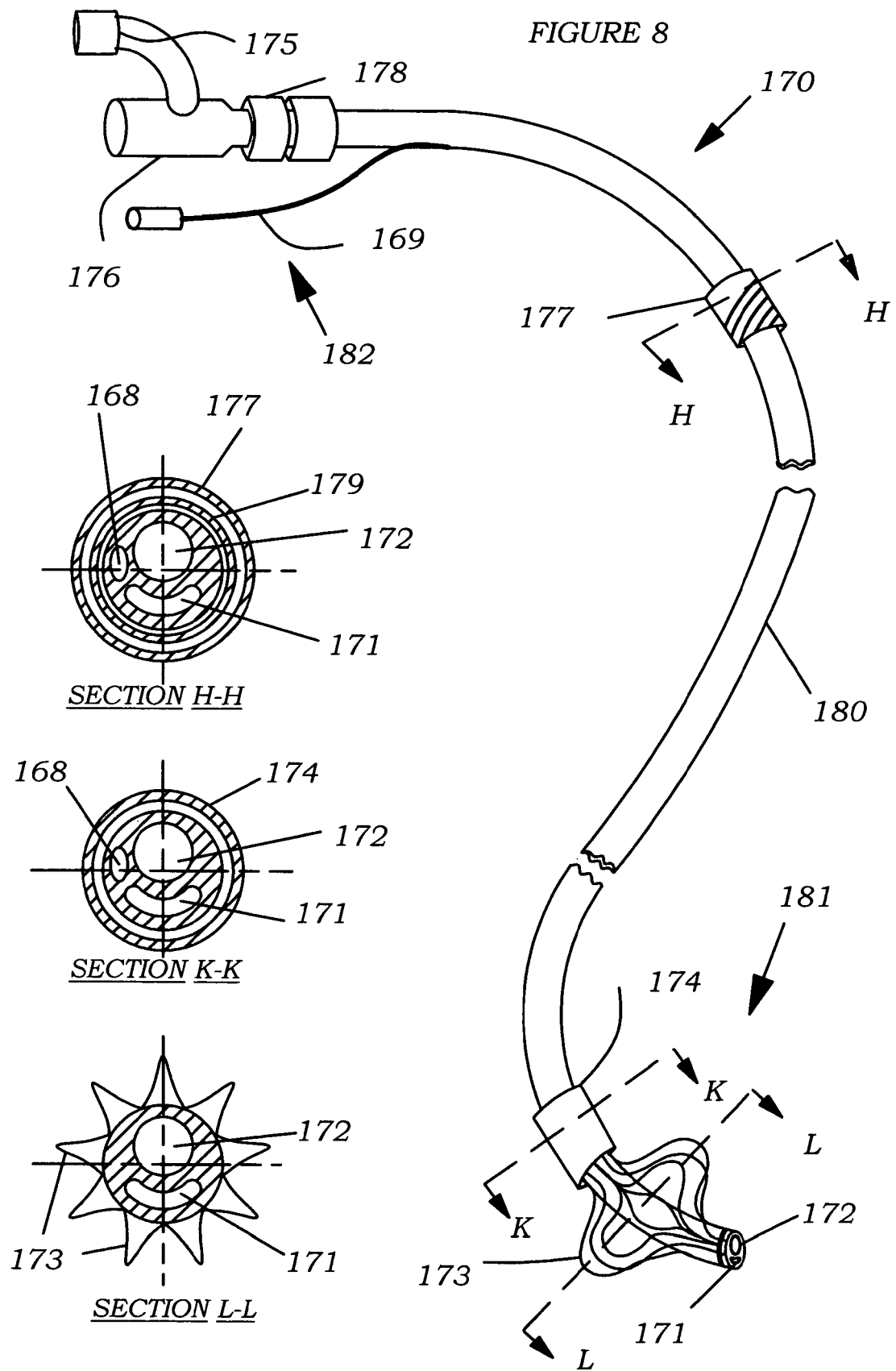
FIG. 8 describes a typical TTSV catheter.

FIG. 8 describes a typical TTSV catheter 170 with a catheter shaft 180 a distal end 181, a proximal end 182, a proximal end connector 176 for attachment to the TTSV Gas Control Unit, connection ports for insufflation flow 175 and suction 176, a distal end anchoring member 173, a slide-able sleeve 177 for placement in the percutaneous incision with a self-sealing gasket 179, a connection 178 for detachment of the proximal end of the catheter, a sleeve 174 for compressing the anchoring member 173, a mechanism 169 for retracting the sleeve 174, a lumen 168 for the mechanism 169, a lumen for gas delivery 171 and a lumen for gas suctioning 172.

FIG. 9 describes typical TTSS catheter configurations. FIG. 9a shows a dual TTSS catheter device, each catheter comprising a shaft 150, a balloon 151, for sealing at the distal tip of the catheter, a connector at the proximal end 152 of the catheter for optional connection to a suction source, a port 153 for inflation of the balloon, a through lumen 154 throughout the length of the catheter for guidewire insertion or for applying suction through the catheter, a 15 mm swivel elbow connector 155 for attachment to an endotracheal tube 156 and breathing circuit 157 and a port 158 for insertion of a bronchoscope if needed.

FIG. 9b shows a dual TTSS catheter integrated into the construction of an endotracheal tube 160. The TTSS catheters are slide-able within lumens 161 and 162 in the wall of the endotracheal tube. The catheters include connectors 163 for inflation of the occlusion balloons 164.

FIG. 10 describes alternate TTSV or TTSS catheter systems, devices and configurations. FIG. 10a shows a catheter with a self expanding woven wire anchor 400 which expands upon retraction of an outer sleeve 401 concentric to the catheter shaft 402. The catheter includes lumens for gas delivery 403 and gas removal 404. FIG. 10b shows a catheter with an inflatable balloon 405 which serves as an anchor and a bronchial occluder. The balloon is either electively inflatable, or is normally inflated and electively deflatable. FIG. 10c describes an inflatable anchor 407 in the shape of radial spokes 408 and hence anchors the catheter tip but does not occlude the bronchus. FIG. 10d describes a catheter with both an occlusive balloon 410 and a non-occlusive anchor 411. FIG. 10e shows a catheter with an inflatable balloon anchor 414 and in which the catheter includes a large port 415 communicating with a lumen 416 such that the anchor does not occlude the bronchus. Gas is free to flow between the treated area 417 and the proximal areas 418 to avoid the clinical problems of complete bronchial obstruction. FIG. 10f describes a catheter anchor comprised of wire loops 420. FIG. 10g describes a catheter with multiple small lumens 422 for gas delivery and a large lumen for gas suctioning 423. FIG. 10h shows a dual lumen catheter comprised of two concentric tubes 425 and 426 forming an inner lumen 427 and annular lumen 428, wherein the inner tube or lumen is recessed from the catheter tip. Suctioning is conducted through the annular lumen and gas delivery through the inner lumen such that the gas delivery can prevent clogging of the suctioning path by flushing out any debris 429. FIG. 10i describes a tri-lumen catheter with a lumen 432 for passage of a guidewire 433 wherein the guidewire may comprise a compressible anchoring feature 434 that can be retracted into the catheter lumen. FIG. 10j shows a dual lumen catheter in which the tip has been shaped to bend one lumen 440 180° such that the end of the lumen 441 points proximally away from the targeted lung area 442. Positive pressure is applied to the proximal end of this lumen to create a high velocity jet 443 at the distal port 441. The jet entrains gas in the targeted area 444 to be sucked out with the jet due to the venturi effect and thus allows for suctioning of gas but without the risk of clogging the catheter with debris. FIG. 10k describes another venturi system in which the tip of the catheter is configured such that positive pressure gas ports 450 are pointed proximally. High velocity gas exiting these ports 451 entrain gas in the targeted area 452 to be sucked out with the jet. These venturi configurations are especially useful in applications where gas removal is critical to the therapy and where there is a risk of catheter clogging if vacuum where to be used.

Figure 11:
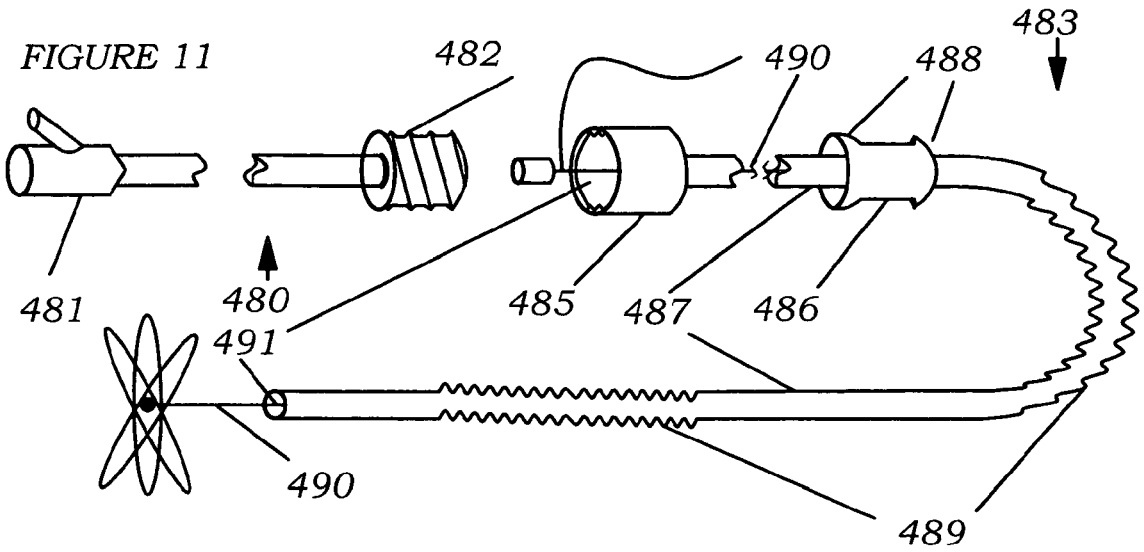
FIG. 11 describes an over-guidewire and exchange catheter configuration.

FIG. 11 describes a catheter exchange system wherein the catheter is placed over a guidewire and can be disconnected. The proximal section 480 or machine end which remains external to the patient, includes a connector 481 for connection to a TTSV ventilation control unit and a connector 482 for removal of the proximal section from the distal section 483. The distal section 483 or patient end which is predominantly inside the body, includes a receiving connector 485 for the proximal end and a slide-able sleeve 486 for placement in the percutaneous incision. The sleeve self-seals on the shaft of the catheter 487 and applies a slight amount of tension to the catheter shaft to prevent inadvertent dislodgment of the catheter from the lung. The sleeve also includes widenings 488 on both ends to anchor it in place on both sides of the incision. The distal section of the catheter also includes a stretchable section of catheter tubing 489 such that during movements of the patient's neck, the catheter length can change without transferring undesired tension to the distal end and inadvertently dislodging the catheter. Also included is a guidewire 490 that can be inserted and removed from a lumen 491 in the catheter, in order to initially place the catheter into the targeted site, or to place in the targeted site while the catheter is being removed, for example for cleaning or replacement.

Typical diameters of the TTSV catheter depend on the lung area being targeted. Some exemplary dimensions follow: Lobar segment: OD=2.0-3.5 mm; Lobar subsegment: OD=1.5-2.5 mm; Lobar sub-subsegment: OD=0.5-1.0 mm. TTSV catheter gas insufflation lumen diameters are typically 0.25-1.0 mm and gas exhaust lumens, if separately present, are typically comprise an area of 0.8-4.0 mm$^2$, preferably greater than 2.0 mm$^2$ to avoid mucous plugging. Catheter lengths are typically 120-150 cm. Anchoring forces are typically 1-10 psi and occlusion forces, if occlusion is utilized, are typically 0.2-0.5 psi. Anchors and occlusive member diameters depend on the targeted bronchial level and are up to 25 mm for main stem bronchus cannulation, 20 mm for lobar bronchus cannulation, 12 mm for segmental bronchi and 3 mm for sub-subsegmental bronchi cannulation when fully expanded. Proximal entry point tensioning forces typically produce 0.5-1.5 lbs of axial tension. The percutaneous plug is typically a soft rubber or thermoset material such as silicone. Some examples of catheter materials are; the shaft extrusion typically comprised of a thermoplastic or thermoset material such as nylon, PVC, polyethylene, PEBAX or silicone; the non-occlusive anchor typically comprised of a stainless steel or Nitinol wire; the inflatable occlusive member comprised of a highly compliant plastisol, silicone or urethane; connectors typically comprised of PVC, polysulfone, polypropylene or acrylic.

Figure 12A:
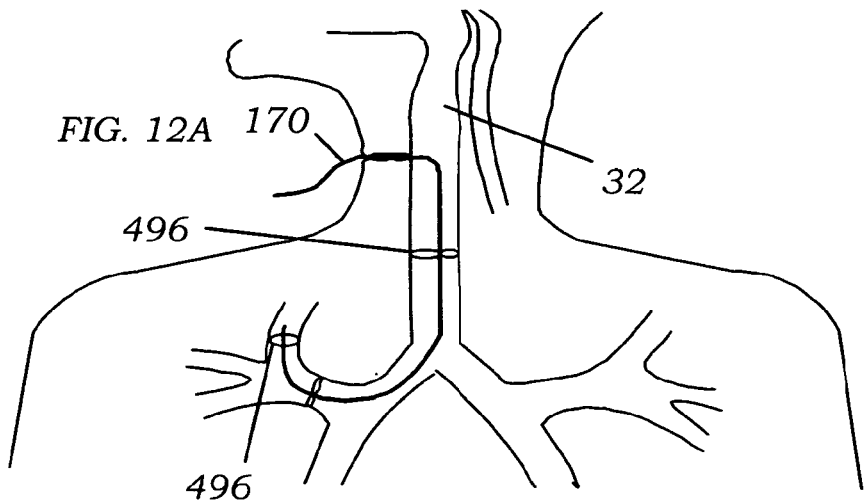
FIG. 12 describes means to allow the TTSV catheter to remain in place without irritating the bronchial walls.
Figure 12B:
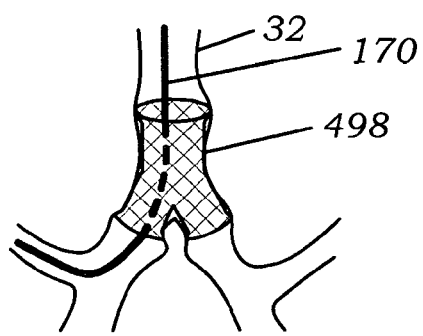
Figure 12C:
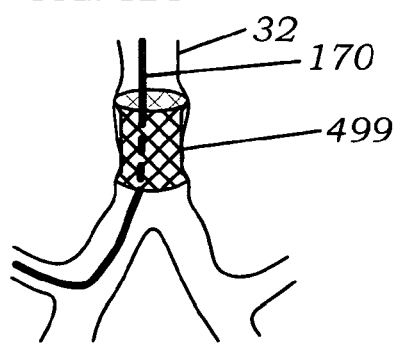

FIG. 12 describes a method and apparatus to allow the indwelling TTSV or TTSS catheter to remain in place for extended periods without irritating the bronchial walls and optionally to prevent dislodgment of the catheter during movement of the neck. FIG. 12a describes compressible loops 496 attached to the catheter 170 which can secure the catheter in place at various places along the tracheal-bronchial tree. The loops also center the catheter so that the catheter does not rub against the trachea 32 or airway walls. FIGS. 12b and 12c describe a bifurcated woven sleeve 498 and cylindrical sleeve 499 to which the catheter 170 is attached to center the catheter in the trachea 32 and airways and to absorb any tension applied to the distal end of the catheter.

Figure 13:
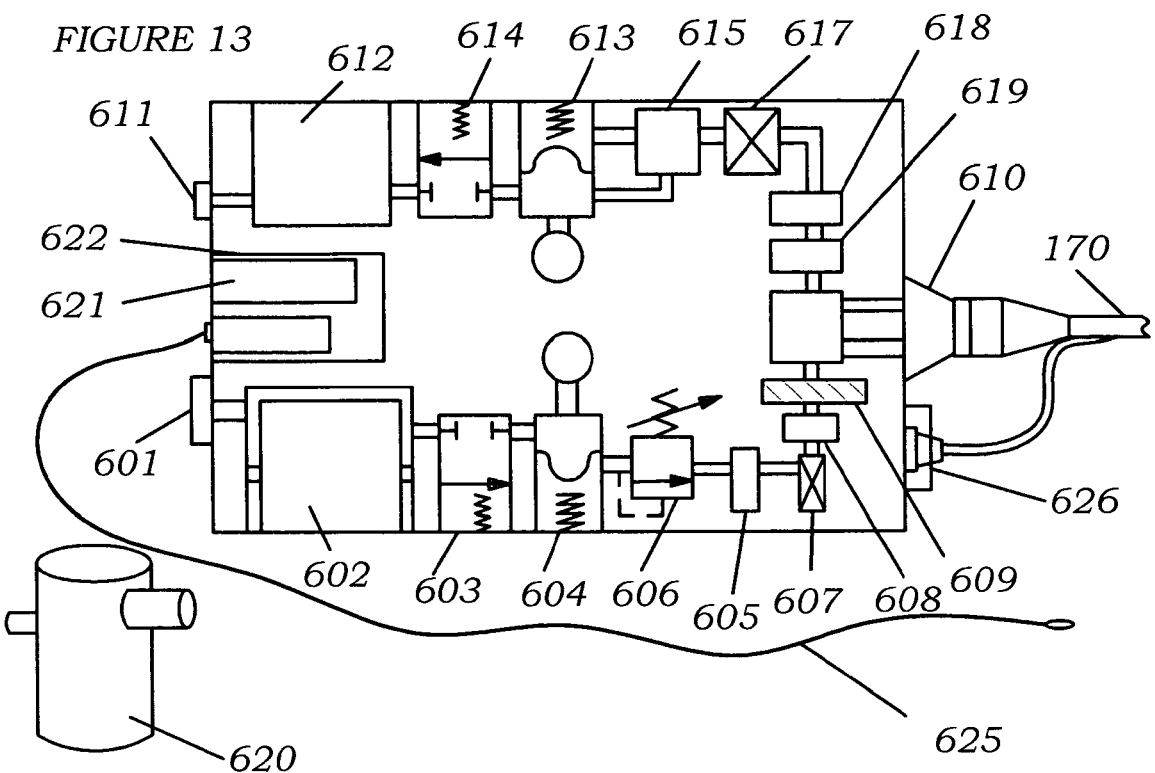
FIG. 13 describes the TTSV Gas Control Unit.

FIG. 13 describes the TTSV Gas Control Unit comprising both positive pressure gas delivery and negative pressure gas removal capability, although the unit may also comprise one or the other function. Shown on the insufflation side is a gas inlet connector 601 for a gas source, a gas reservoir or gas pressure pump 602, an insufflation pressure regulation valve 604, an on-off control valve 603, a pilot valve 605 for relaying a desired pressure reference to the pressure regulating valve with closed loop feedback control for proper pressure output, an over-pressure safety relief valve 606, a check valve 607, a pressure sensor 608, a gas outlet filter 609, and a TTSV catheter connector 610. Shown on the suction side is a vacuum source inlet connector 611, a vacuum reservoir or vacuum generation pump 612, a vacuum level regulation valve 613, an on-off control valve 614, vacuum pressure pilot pressure valve 615, a check valve 617, pressure sensor 618 and $CO_2$ sensor 619. A replaceable or refillable modular cartridge of ventilation gas 620 is shown as an alternative supply, typically housing 100-500 ml of compressed ventilation gas. For example a cartridge containing 250 ml of compressed gas pressurized at 10 psi would enable delivery of gas at a rate of 10 ml/hour at an average output pressure of 25 $cmH_2O$ for 20 days, based on ideal gas laws, and assuming 30% losses due to system leakage. Also shown is a power supply 621, and electrical circuitry 622 containing the signal processing, command center, microprocessor and imbedded software, a communication bus for inputs and outputs to and from the valves, sensors and user interface. An optional respiration sensor 625 is shown which controls or synchronizes the TTSV parameters if so desired. An optional control module 626 for controlling inflating and deflating the occlusive member at the distal tip of the catheter, if so equipped, is also shown. In other embodiments, the patient can use their own suction power generated by their lung for gas removal from the targeted area, for example by coupling their mouth to the proximal end of the catheter.

Figure 14:
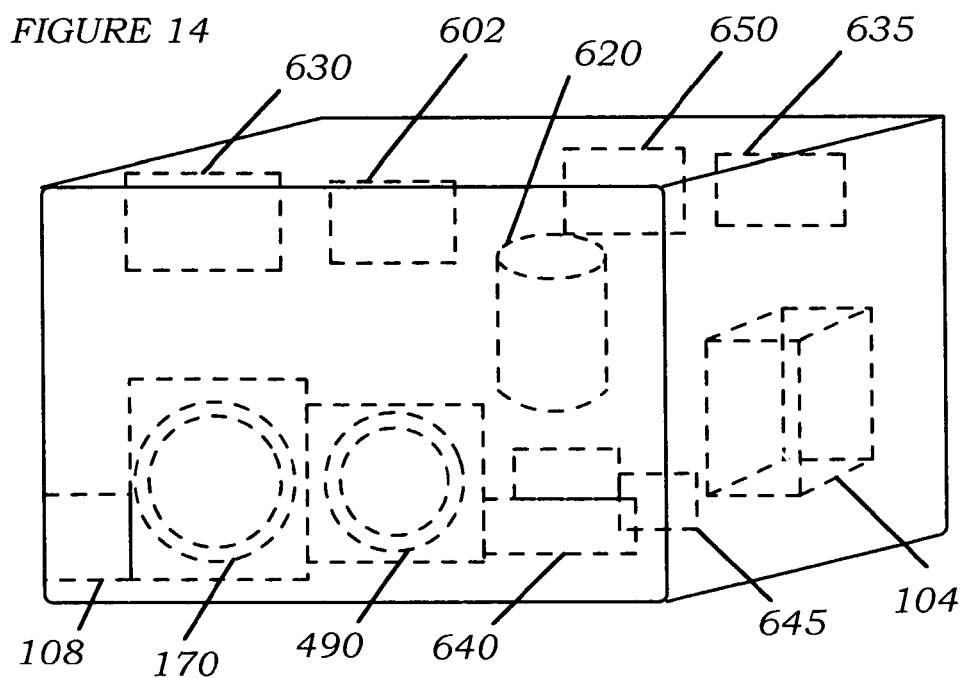
FIG. 14 describes a TTSV Kit.

FIG. 14 describes a kit including a sterile TTSV catheter assembly 170, a sterile guidewire 490, a percutaneous incision and dilitation kit 630, an access port plug 108, a Gas Control Unit 104, a gas cartridge 620, a holster for the Gas Control Unit 635, spare battery 602 and wall charger 640, cleaning supplies 645, instruction guide 650.

The invention claimed is:

1. An apparatus for the purpose of directly ventilating a lung area of a patient, the apparatus comprising:
   a. a catheter with a distal and proximal end with at least one lumen for fluid flow, comprising:
      i. at its distal end an anchoring means to anchor said distal end of said catheter in a bronchial lumen;
      ii. at its proximal end a connection means for connection to a ventilation control source external to the patient;
      iii. between said distal and proximal ends a securing means concentric with a shaft of said catheter for sealing, tensioning and connecting said shaft to the entry point of said catheter into the body of the patient;
   b. a ventilation gas control unit comprising:
      i. a ventilation gas supply, and comprising an output connection means for connection of said proximal end of said catheter and comprising a coupling means to couple said ventilation gas supply with a fluid lumen of said catheter, and comprising a ventilation measurement and regulation means to produce and regulate a desired output of said ventilation gas supply;
      a vacuum supply, and comprising a connection means for connection of said proximal end of said catheter and comprising a coupling means to couple said vacuum supply with said fluid lumen of said catheter, and further comprising a vacuum measurement and regulation means to produce and regulate a desired output of said vacuum supply;
      iii. a user interface for selection of the desired output and ventilation parameters and for displaying selected, measured and regulated input and output parameters;
      iv. a gas concentration measuring means.

2. An apparatus as in claim 1 wherein said anchoring means is a non-occlusive member.

3. An apparatus as in claim 1 wherein said catheter further comprises an outer sleeve axially slidable about said shaft of said catheter, and wherein said anchoring means is compressed between said shaft and said outer sleeve, and wherein axial retraction of said outer sleeve releases said anchor anchoring means to expand.

4. An apparatus as in claim 1 wherein said anchoring means comprises a clip member, said clip configured for attachment to a bronchial bifurcation or septum.

5. An apparatus as in claim 1 wherein said anchoring means comprises an occlusive member.

6. An apparatus as in claim 1 wherein said distal end of said catheter includes an occlusive member to occlude a bronchus and a non-occlusive anchor to anchor said catheter in a bronchus.

7. An apparatus as claim 1 wherein said catheter comprises a lumen in which a guiding member is placed, and wherein said guiding member includes said anchoring means at its distal end wherein said anchoring means protrudes from the distal tip of said catheter.

8. An apparatus as in claim 1 wherein said catheter further comprises at least two lumens, one for gas delivery and one for gas removal by vacuum.

9. An apparatus as in claim 1 wherein said securing means is configured to seal and secure said catheter to a percutaneous access site.

10. An apparatus as in claim 1 wherein at least the distal end of said catheter comprises a plurality of branches wherein said branches are configured for cannulating multiple bronchi simultaneously.

11. An apparatus as in claim 1 wherein at least one said catheter is movably slidable in at least one lumen in a tracheal tube.

12. An apparatus as in claim 1 wherein a length of said catheter is 25 to 300 cm.

13. An apparatus as in claim 1 wherein said catheter futher comprises an extruded thermoplastic or thermoset tubular material construction.

14. An apparatus as in claim 1 comprising a port near said distal end of said catheter, said port directed proximally away from targeted lung area, wherein said port communicates with a lumen in said catheter, said lumen connected to a pressurized gas source, and wherein said ventilation gas control unit delivers a pressurized gas to said lumen thus entraining gas in said targeted area to be exhausted proximally with said pressurized gas.

15. An apparatus as in claim 1 integral to or re-movably attachable to a mechanical ventilator.

16. An apparatus as in claim 1 comprising features for portability and wearability by the user selected from the group consisting of an internal battery, an internal pressurized gas source, an internal vacuum source, a belt clip, a fanny pack and a shoulder strap.

17. An apparatus as in claim 1 comprising a replaceable or refillable ventilation gas cartridge.

18. An apparatus as in claim 1 wherein the gas concentration measuring means is configured to measure $CO_2$ concentration of gas removed from the lung area of the patient.

19. An apparatus as in claim 1 further comprising a kit, the kit comprising a ventilation catheter with sleeve connector, an access incision plug, a guiding catheter, a gas control unit, a quantity of ventilation gas, a portable case, a spare battery and battery charger, cleaning supplies, a hygienic seal for sealing distal section of catheter when proximal section is removed, and an instruction sheet.

20. A system for site-specific ventilation of an area of a lung of a patient, comprising:
   an indwelling catheter adapted to be disposed in a bronchus of a poorly ventilated lung area to provide direct ventilation to that area, the indwelling catheter including at least one lumen, a distal end and a proximal end;
   an anchor disposed on the distal end of the catheter, the anchor being adapted to dilate a bronchus to secure the indwelling catheter in position for an extended time;
   a gas control unit coupled to the catheter to control flow through the lumen of the catheter;
   a gas delivery system coupled to the catheter and the gas control unit, the gas delivery system being adapted to provide ventilation gas through the lumen of the catheter to the area of the lung;
   a gas removal vacuum system coupled to the catheter and the gas control unit, the gas removal system being adapted to suction $CO_2$ rich stagnant gas from the area of the lung through the lumen of the catheter,
   wherein the gas control unit is adapted to control the gas removal and delivery systems to deliver and suction gas through the catheter to and from the area of the lung without total lung mechanical ventilation and without collapsing the area of the lung; and
   a patient respiration sensor coupled to the gas control unit to synchronize the gas delivery system and the gas removal system to a patient's spontaneous inspiratory phase and expiratory phase.

21. An apparatus for the purpose of directly ventilating a lung area of a patient, the apparatus comprising:
   a. a catheter with a distal and proximal end with at least one lumen for fluid flow, comprising:
      i. at its distal end an anchoring means to anchor said distal end of said catheter in a bronchial lumen;
      ii. at its proximal end a connection means for connection to a ventilation control source external to the patient;
      iii. between said distal and proximal ends a securing means concentric with a shaft of said catheter for sealing, tensioning and connecting said shaft to the entry point of said catheter into the body of the patient;
      iv. an outer sleeve axially slidable about said shaft, wherein said anchoring means is compressed between said shaft and said outer sleeve, and wherein axial retraction of said outer sleeve releases said anchoring means to expand;
   b. a ventilation gas control unit comprising:
      i. a ventilation gas supply, and comprising an output connection means for connection of said proximal end of said catheter and comprising a coupling means to couple said ventilation gas supply with a fluid lumen of said catheter, and comprising a ventilation measurement and regulation means to produce and regulate a desired output of said ventilation gas supply;
      ii. a vacuum supply, and comprising a connection means for connection of said proximal end of said catheter and comprising a coupling means to couple said vacuum supply with said fluid lumen of said catheter, and further comprising a vacuum measurement and regulation means to produce and regulate a desired output of said vacuum supply;
      iii. a user interface for selection of the desired output and ventilation parameters and for displaying selected, measured and regulated input and output parameters.

22. An apparatus for the purpose of directly ventilating a lung area of a patient, the apparatus comprising:
   a. a catheter with a distal and proximal end with at least one lumen for fluid flow, comprising:
      i. at its distal end an occlusive member to occlude a bronchus and a non-occlusive anchor to anchor said catheter in a bronchus;
      ii. at its proximal end a connection means for connection to a ventilation control source external to the patient;
      iii. between said distal and proximal ends a securing means concentric with a shaft of said catheter for sealing, tensioning and connecting said shaft to the entry point of said catheter into the body of the patient;
   b. a ventilation gas control unit comprising:
      i. a ventilation gas supply, and comprising an output connection means for connection of said proximal end of said catheter and comprising a coupling means to couple said ventilation gas supply with a fluid lumen of said catheter, and comprising a ventilation measurement and regulation means to produce and regulate a desired output of said ventilation gas supply;
      ii. a vacuum supply, and comprising a connection means for connection of said proximal end of said catheter and comprising a coupling means to couple said vacuum supply with said fluid lumen of said catheter, and further comprising a vacuum measurement and regulation means to produce and regulate a desired output of said vacuum supply;
      iii. a user interface for selection of the desired output and ventilation parameters and for displaying selected, measured and regulated input and output parameters.

\* \* \* \* \*